(12) United States Patent
Hou et al.

(10) Patent No.: US 10,093,694 B2
(45) Date of Patent: *Oct. 9, 2018

(54) COMPOUNDS FOR TREATING EYE DISORDERS OR DISEASES

(71) Applicants: Guangzhou KangRui Biological Pharmaceutical Technology Co, Ltd., Guangzhou (CN); The Regents of the University of California, Oakland, CA (US)

(72) Inventors: Rui Hou, Guangzhou (CN); Kang Zhang, San Diego, CA (US); Gen Li, Guangzhou (CN)

(73) Assignees: GUANGZHOU KANGRUI BIOLOGICAL PHARMACEUTICAL TECHNOLOGY CO, LTD., Guangzhou (CN); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/423,359

(22) Filed: Feb. 2, 2017

(65) Prior Publication Data

US 2017/0218009 A1 Aug. 3, 2017

Related U.S. Application Data

(60) Provisional application No. 62/290,837, filed on Feb. 3, 2016.

(51) Int. Cl.
| | |
|---|---|
| *C07J 9/00* | (2006.01) |
| *C07J 17/00* | (2006.01) |
| *C07J 33/00* | (2006.01) |
| *C07J 51/00* | (2006.01) |

(52) U.S. Cl.
CPC ............... *C07J 9/00* (2013.01); *C07J 17/00* (2013.01); *C07J 33/002* (2013.01); *C07J 51/00* (2013.01)

(58) Field of Classification Search
CPC .................................. C07J 9/00; C07J 17/00
See application file for complete search history.

(56) References Cited

U.S. PATENT DOCUMENTS 9,675,623 B2 * 6/2017 Gestwicki ............ A61K 31/045

FOREIGN PATENT DOCUMENTS

| JP | 2009249316 A | 10/2009 |
|---|---|---|
| JP | 2011246464 A | 12/2011 |
| WO | WO-2014117710 A1 | 8/2014 |

OTHER PUBLICATIONS

Science Jul. 23, 2015.*
Canedella (Survey of ophthalmology, 40(4) 1996 (320-337).*
Berge et al. Pharmaceutical Salts. Journal of Pharmaceutical Sciences 66(1):1-19 (Jan. 1977).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).
Aoyama et al. Structural analysis of the interaction between the side-chain of substrates and the active site of lanosterol 14 alpha-demethylase (P-450(14)DM) of yeast. Biochim Biophys Acta 1122(3):251-255 (1992).
Parish et al. Studies of the oxysterol inhibition of tumor cell growth. Steroids 53(3-5):579-596 (1989).
PCT/US2017016215 International Search Report and Written Opinion dated May 23, 2017.
Shingate et al. Synthesis and antimicrobial activity of novel oxysterols from lanosterol. Tetrahedron 69(52):11155-11163 (2013).

* cited by examiner

*Primary Examiner* — Shirley V Gembeh
(74) *Attorney, Agent, or Firm* — Wilson, Sonsini, Goodrich & Rosati

(57) ABSTRACT

Described herein are compounds that inhibit or prevent protein aggregation, methods of making such compounds, pharmaceutical compositions and medicaments comprising such compounds, and methods of using such compounds in the treatment of conditions, diseases, or disorders associated with protein aggregation.

18 Claims, 26 Drawing Sheets

4°C over night

Room Temperature 4h

4°C over night

Room Temperature 4 h

COMPOUNDS FOR TREATING EYE DISORDERS OR DISEASES

CROSS-REFERENCE

This application claims the benefit of U.S. Provisional Application No. 62/290,837, filed Feb. 3, 2016, the content of which is hereby incorporated by reference in its entirety.

BACKGROUND OF THE DISCLOSURE

Affecting tens of millions of people, cataracts are the most common cause of blindness worldwide. The current and only course of treatment is eye surgery to remove the affected lens. This type of invasive procedure is not ideal in developing countries where access to surgical care is limited; and as such, cataracts are associated with higher morbidity in such places. In developed nations, surgical removal is also not ideal as the sheer prevalence of the disease among the ageing population means that cataract surgeries amount to a significant portion of healthcare costs. As such, there exists a need to develop new treatments for treating cataracts that do not require surgery.

Protein aggregation has been implicated as one of the primary contributory factors for cataract formation. Described herein are compounds that inhibit or prevent protein aggregation.

SUMMARY OF THE DISCLOSURE

In one aspect, provided herein is a compound of Formula (Ic):

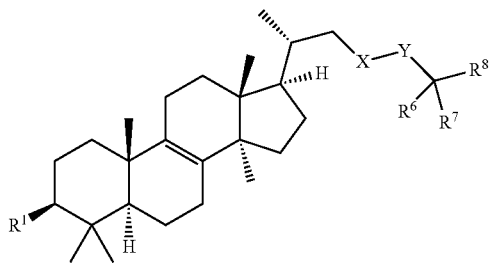

Formula (Ic)

or a pharmaceutically acceptable salt thereof,
wherein
X is —C($R^4$)$_2$—;
each $R^4$ is independently hydrogen, —$OR^e$, optionally substituted $C_1$-$C_6$alkyl, or halogen; each $R^e$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;
Y is —C($R^5$)$_2$—;
each $R^5$ is independently hydrogen, —$OR^g$, optionally substituted $C_1$-$C_6$alkyl, or halogen;
$R^g$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;
each $R^6$, $R^7$, and $R^8$ is independently hydrogen, optionally substituted $C_1$-$C_6$alkyl, halogen, —$OR^h$, —$SR^h$, or —N($R^i$)$_2$;
each $R^h$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;
each $R^i$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^i$ are taken together with the N atom to which they are attached to form an optionally substituted heterocycloalkyl ring;
$R^1$ is —$OR^{10}$, —$SR^{10}$, —N($R^{10}$)$_2$, or halogen; and
each $R^{10}$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycloalkyl ring.

In some embodiments, X is —$CH_2$— or —CH($OR^e$)—. In some embodiments, $R^e$ is hydrogen. In some embodiments, Y is —$CH_2$—, —CH($OR^g$)—, or —CH($R^5$)—; and $R^5$ is optionally substituted $C_1$-$C_6$alkyl or halogen. In some embodiments, $R^g$ is hydrogen. In some embodiments, $R^5$ is —Br or —F. In some embodiments, $R^5$ is methyl or ethyl. In some embodiments, $R^6$ and $R^7$ are each independently $C_1$-$C_3$ alkyl. In some embodiments, $R^6$ and $R^7$ are each independently methyl. In some embodiments, $R^8$ is hydrogen, —$OR^h$, or —N($R^i$)$_2$.

In some embodiments, the compound disclosed herein, or the pharmaceutically acceptable salt thereof, has a Formula (Id):

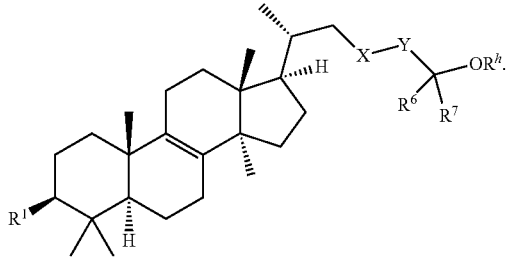

Formula (Id)

In some embodiments, $R^h$ is hydrogen.

In some embodiments, the compound disclosed herein, or the pharmaceutically acceptable salt thereof, wherein the compound is selected from:

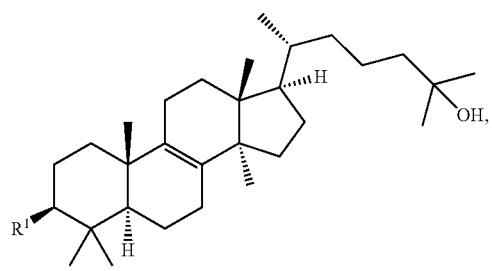

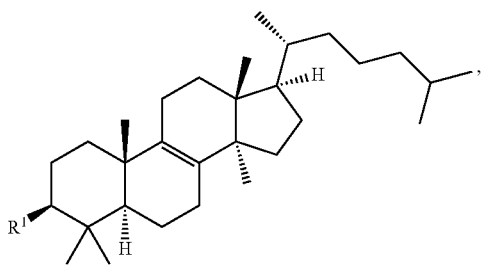
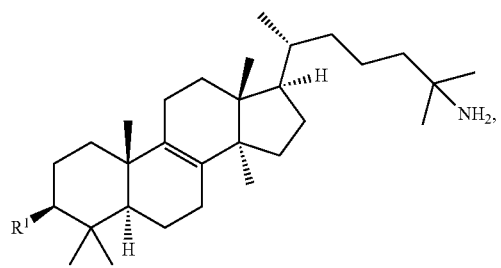
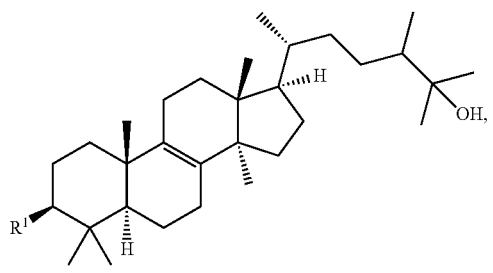
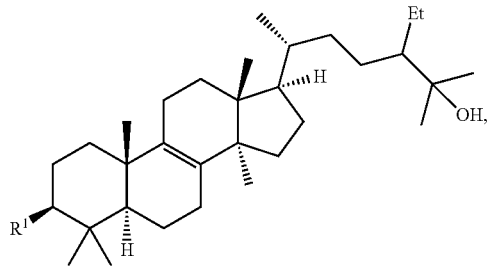
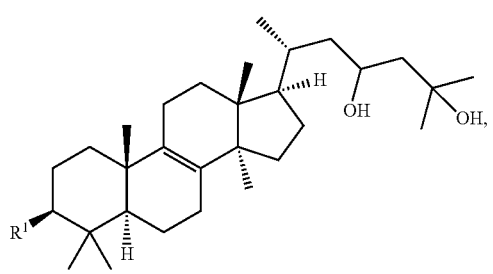
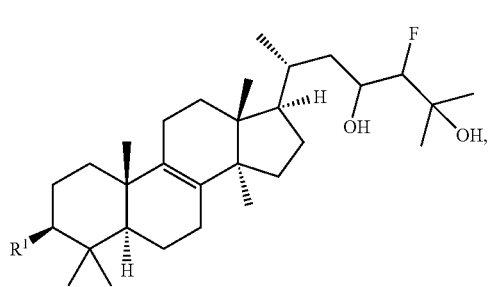
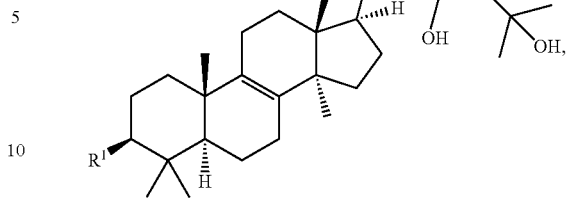
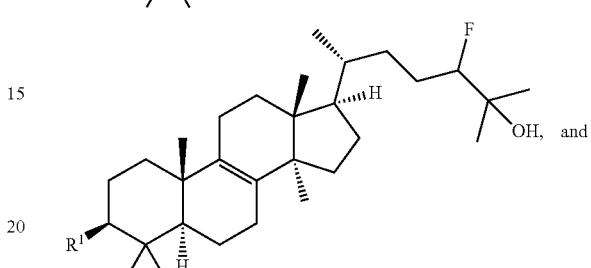
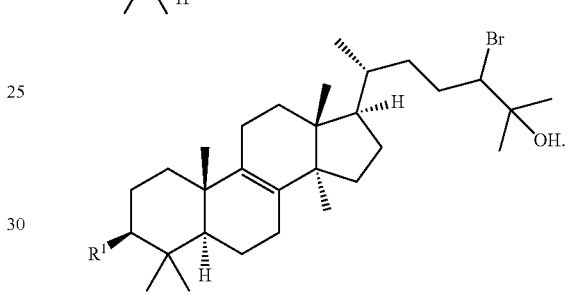
In some embodiments, $R^1$ is —$OR^{10}$. In some embodiments, $R^1$ is —OH, —OMe, —OEt, or —O-n-Pr. In some embodiments, $R^1$ is —OH. In some embodiments, $R^1$ is —$SR^{10}$, or —$N(R^{10})_2$. In some embodiments, $R^1$ is —$NH_2$, —NH(Me), —$N(Me)_2$, —NH(Et), or —SH. In some embodiments, $R^1$ is halogen. In some embodiments, $R^1$ is —Br.
In some embodiments, the compound disclosed herein is selected from:
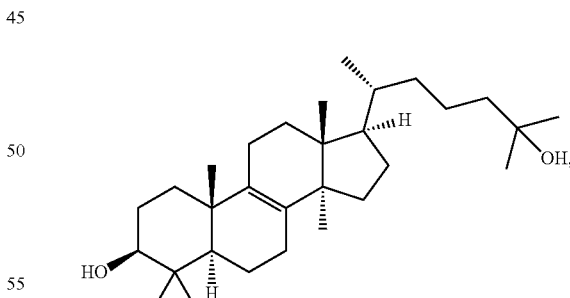
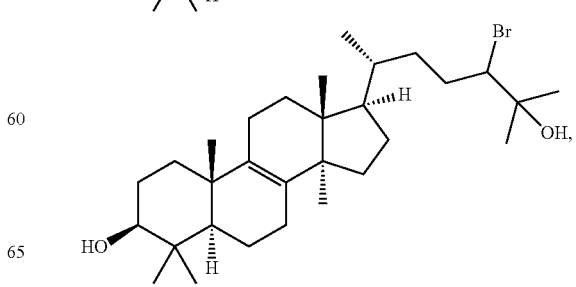

-continued

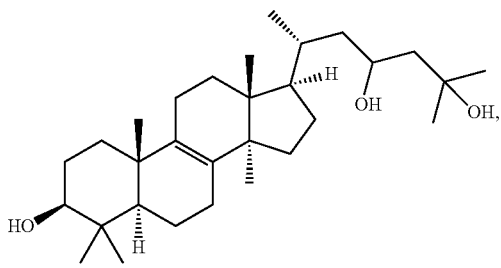

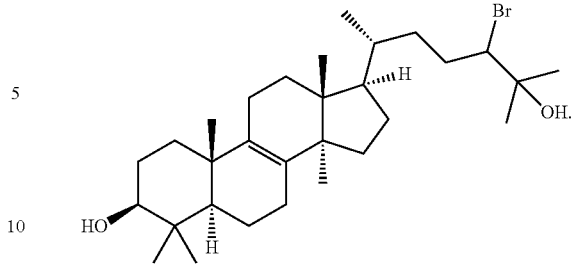

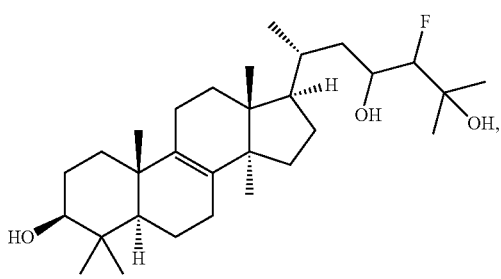

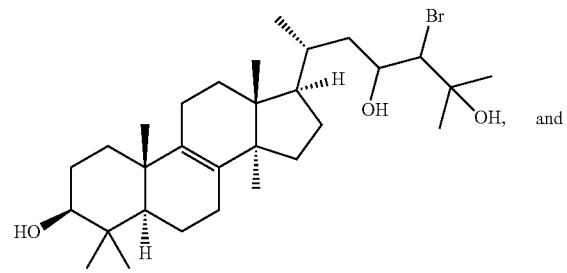

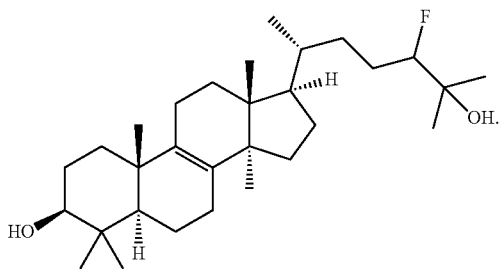

In some embodiments, the compound disclosed herein is selected from:

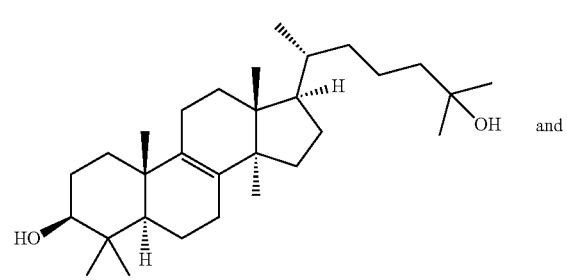

In another aspect, provided herein is a pharmaceutical composition comprising any one of the compounds disclosed herein or a pharmaceutically acceptable salt thereof, and a pharmaceutically acceptable excipient.

In another aspect, provided herein is a method of treating a disease or disorder in a subject in need thereof, comprising administering a therapeutically effective amount of any one of the compounds disclosed herein, or a pharmaceutically acceptable salt thereof. In some embodiments, the disease or disorder is an eye disease or disorder. In some embodiments, the eye disease or disorder is selected from the group consisting of cataract, congenital cataracts, cortical opacities, posterior subcapsular cataract, presbyopia nuclear sclerosis, retinal degenerative disorder, Refsum disease, Smith-Lemli-Opitz syndrome, Schnyder crystalline corneal dystrophy, drusen, age-related macular degeneration, and diabetic retinopathy. In some embodiments, the compound, or the pharmaceutically acceptable salt thereof, inhibits or prevents protein aggregation. In some embodiments, the protein is an amyloid-forming protein. In some embodiments, the amyloid-forming protein is selected from Hsp27, αA-crystallin, αB-crystallin, ßB2-crystallin, ßB1-crystallin, γD-crystallin, Hsp22, Hsp20, tau, alpha-synuclein, IAPP, beta-amyloid, PrP, huntingtin, calcitonin, atrial natriuretic factor, apolipoprotein AI, serum amyloid A, medin, prolactin, transthyretin, lysozyme, beta 2 microglobulin, gelsolin, keratoepithelin, cystatin, immunoglobulin light chain AL, and S-IBM. In some embodiments, the protein is a protein underlying a loss of function disease. In some embodiments, the protein underlying a loss of function disease is selected from the group consisting of mutant ß-glucosidase, cystic fibrosis transmembrane receptor, hexosaminidase A, hexosaminidase B, ß-galactosidase, and alpha-glucosidase.

Also provided herein is method of treating and/or preventing an eye disease or disorder in a subject in need thereof, comprising administering a therapeutically effective amount of any one of the compounds disclosed herein. In some embodiments, the subject is having or at risk of developing an eye disease or disorder that affects the normal structure of the lens in the eye. In some embodiments, the eye disease or disorder is selected from the group consisting of cataracts, congenital cataracts, cortical opacities, posterior subcapsular cataracts, presbyopia, nuclear sclerosis, retinal degenerative disorder, Refsum disease, Smith-Lemli-Opitz syndrome, Schnyder crystalline corneal dystrophy, drusen, age-related macular degeneration, and diabetic retinopathy. In some embodiments, the compound, or the pharmaceutically acceptable salt thereof, inhibits crystallin protein aggregation.

Also provided herein is a method of treating cataract or blindness/impaired vision in a subject in need thereof, comprising administering a therapeutically effective amount of any one of compounds disclosed herein. In some embodiments, the compound dissolves the lens crystallin protein aggregate(s) in the eye of the said subject. In some embodiments, the lens crystallin protein aggregate is α-crystallin, ß-crystallin, or γ-crystallin.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows the $^1$H NMR of the mixture of LS-1 and LS-2 while FIG. 1B shows the $^{13}$C NMR of the mixture of LS-1 and LS-2.

FIG. 2A shows the $^1$H NMR of LS-6 while FIG. 2B shows the $^{13}$C NMR of LS-6.

FIG. 3A shows the $^1$H NMR of LS-2 while FIG. 3B shows the $^{13}$C NMR of LS-2.

FIG. 4A shows the $^1$H NMR of Compound 2 while FIG. 4B shows the $^{13}$C NMR of Compound 2.

FIG. 5A is the MS spectra acquired and FIG. 5B is the MS observed from the fragmentation of the peak at 427.16.

FIG. 6A shows the $^1$H NMR of LS-7 while FIG. 6B shows the $^{13}$C NMR of LS-7.

FIG. 7A shows the $^1$H NMR of Compound 1 while FIG. 7B shows the $^{13}$C NMR of Compound 1.

FIG. 14A show mouse lenses (white) that were dissected from the eye and placed into phosphate buffered saline solution (PBS) overnight at 4° C. FIG. 14B shows the mouse lenses after treatment with Compound 1 for 4 hours at room temperature at the indicated concentrations.

FIG. 15A show mouse lenses (white) that were dissected from the eye and placed into phosphate buffered saline solution (PBS) overnight at 4° C. FIG. 15B shows the mouse lenses after treatment with Compound 2 for 4 hours at room temperature at the indicated concentrations.

FIG. 16A shows the negative control and FIG. 16B shows the treated eye, which shows increased clarity and reduced cataract.

DETAILED DESCRIPTION OF THE DISCLOSURE

Certain Terminology

Figure 1A:
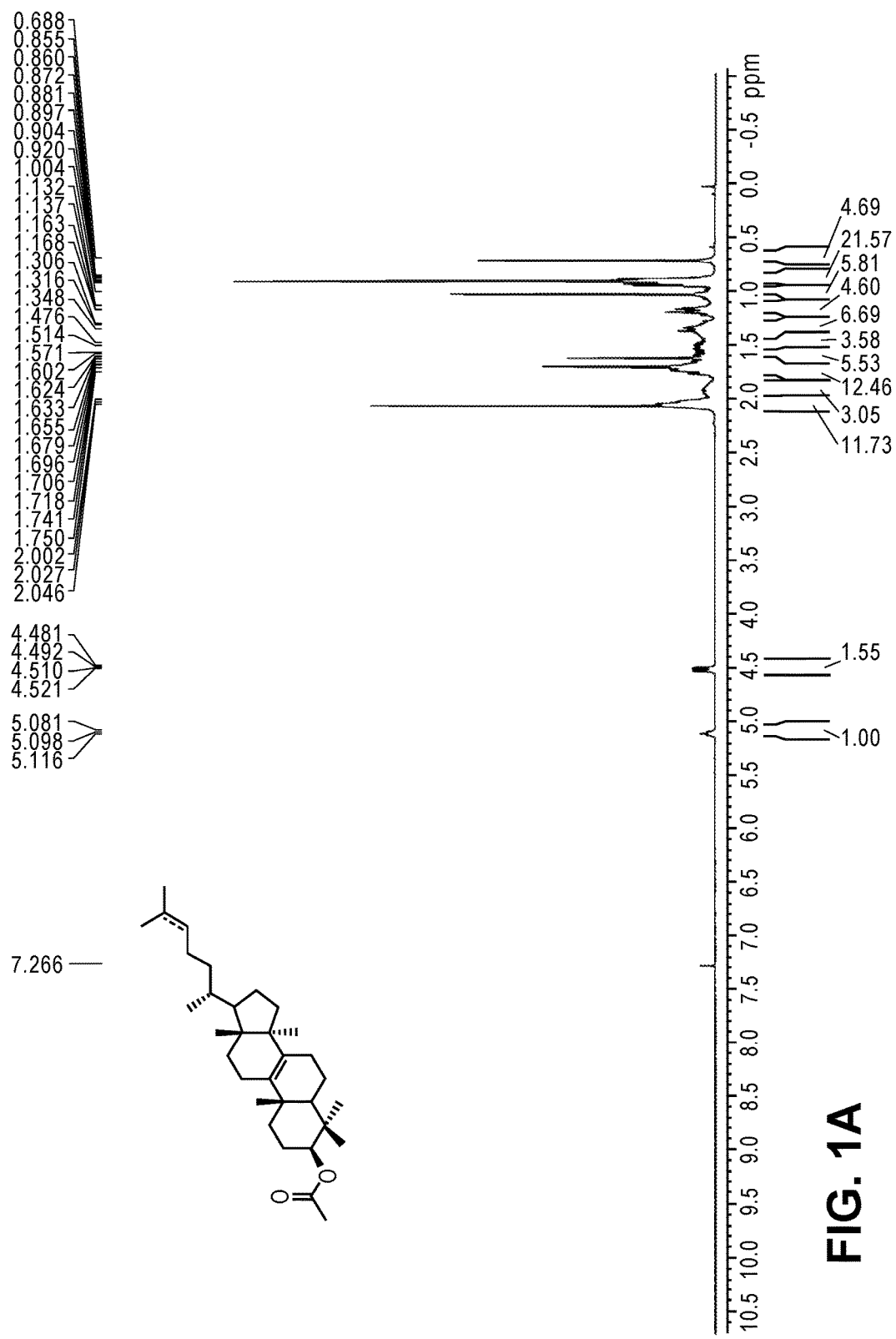
FIGS. 1A and 1B show the NMR data of the mixture of LS-1 and LS-2.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms, or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. In some instances, any of the above mentioned monovalent alkyl groups is an alkylene by abstraction of a second hydrogen atom from the alkyl. In some embodiments, an alkelene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The term "alkenyl" refers to a type of alkyl group in which at least one carbon-carbon double bond is present. In one embodiment, an alkenyl group has the formula —$C(R)$=$CR_2$, wherein R refers to the remaining portions of the alkenyl group, which is the same or different in some embodiments. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —$CH=CH_2$, —$C(CH_3)=CH_2$, —$CH=CHCH_3$, —$C(CH_3)=CHCH_3$, and —$CH_2CH=CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$—C≡$CCH_2CH_3$, —$CH_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. In some embodiments, cycloalkyl groups include groups having from 3 to 10 ring atoms. In some embodiments, cycloalkyl groups include groups having from 3 to 6 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl, and bicycle[1.1.1] pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

The term "cycloalkylene" refers to a monocyclic or polycyclic aliphatic, non-aromatic divalent radical, wherein each of the atoms forming the ring (i.e. skeletal atoms) is a carbon atom. In some embodiments, cycloalkylene are spirocyclic or bridged compounds. In some embodiments, cycloalkylenes are optionally fused with an aromatic ring, and the point of attachment is at a carbon that is not an aromatic ring carbon atom. In some embodiments, cycloalkylene groups include groups having from 3 to 10 ring atoms. In some embodiments, cycloalkylene groups include groups having from 3 to 6 ring atoms.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluralkyl is a $C_1$-$C_6$fluoroalkyl.

The term "fluoroalkyl" refers to an alkyl in which one or more hydrogen atoms are replaced by a fluorine atom. In one aspect, a fluralkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heteroalkylene" refers to an alkylene group in which one or more skeletal atoms of the alkylene are selected from an atom other than carbon, e.g., oxygen, nitrogen (e.g. —NH—, —N(alkyl)-, sulfur, or combinations thereof. In some embodiments, a heteroalkylene is attached to the rest of the molecule at a carbon atom of the heteroalkylene. In one aspect, a heteroalkylene is a $C_1$-$C_6$heteroalkylene.

As used herein, the term "heteroatom" refers to an atom of any element other than carbon or hydrogen. In some embodiments, the heteroatom is nitrogen, oxygen, or sulfur. In some embodiments, the heteroatom is nitrogen or oxygen. In some embodiments, the heteroatom is nitrogen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S, and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic, or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl, or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen, and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms, and 0-1 S atoms in the ring.

The term "bond" or "single bond" refers to a chemical bond between two atoms, or two moieties when the atoms joined by the bond are considered to be part of larger substructure. In one aspect, a single bond refers to a chemical bond between two chemical elements that involves two bonding electrons. A double bond as used herein refers to a chemical bond between two chemical elements involving four bonding electrons. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic, and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylac-

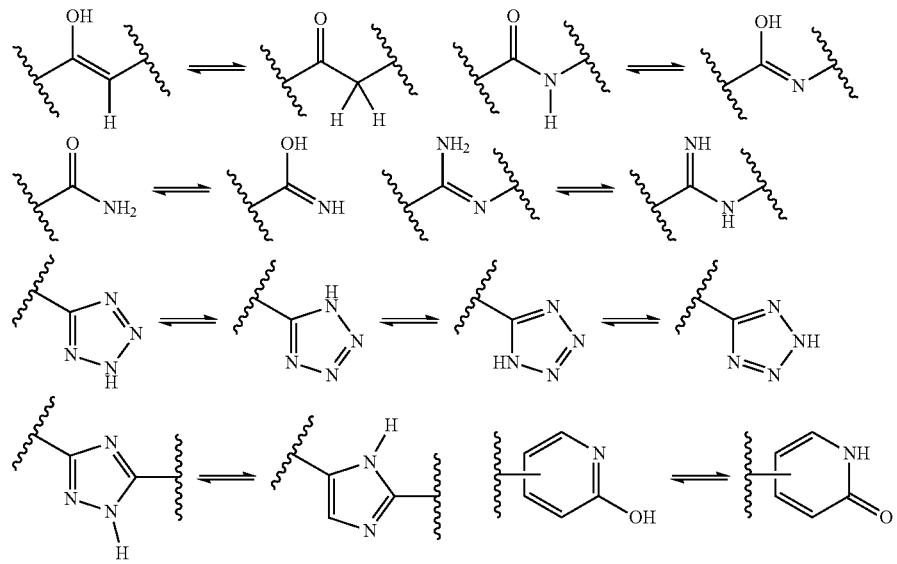

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of etates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). In some embodiments, acid addition salts of basic compounds is be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is converted under physiological conditions or by solvolysis to a biologically active compound described herein in some embodiments. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. In some embodiments, prodrugs of an active compound, as described herein, are be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that are used to enable delivery of compounds or compositions to the desired site of biological action in some instances. These methods include, but are not limited to oral routes, intraduodenal routes, parenteral injection (including intravenous, subcutaneous, intraperitoneal, intramuscular, intravascular or infusion), and topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder in some embodiments. For prophylactic benefit, the compositions are, in some instances, administered to a patient at risk of developing a particular disease, or to a patient reporting one or more of the physiological symptoms of a disease, even though a diagnosis of this disease has not been made in some embodiments.

Protein Aggregation

The lens is comprised of high concentrations of crystallin proteins that are essential for maintaining lens transparency and refractive properties. Cataracts arise when these crystallin proteins aggregate, which leads to loss of lens transparency and opacification. In fact, protein aggregation has been implicated as one of the important factors in cataract formation. The precise mechanisms in which crystallin proteins aggregate and cause opacification are yet to be completely elucidated; however, oxidative stress has been implicated in age-related cataracts and mutations in crystallin proteins have been implicated in congenital cataracts.

In some embodiments, the compounds disclosed herein inhibit or prevent protein aggregation. In some embodiments, the protein is an amyloid-forming protein. In some embodiments, the amyloid-forming protein is selected from Hsp27, αA-crystallin, αB-crystallin, ßB2-crystallin, ßB1-crystallin, γD-crystallin, Hsp22, Hsp20, tau, alpha-synuclein, IAPP, beta-amyloid, PrP, huntingtin, calcitonin, atrial natriuretic factor, apolipoprotein AI, serum amyloid A, medin, prolactin, transthyretin, lysozyme, beta 2 microglobulin, gelsolin, keratoepithelin, cystatin, immunoglobulin light chain AL, and S-IBM. In some embodiments, the amyloid-forming protein is selected from αA-crystallin, αB-crystallin, ßB2-crystallin, ßB1-crystallin, or γD-crystallin.

In some embodiments, the protein is a protein underlying a loss of function disease. In some embodiments, the protein underlying a loss of function disease is selected from the group consisting of mutant ß-glucosidase, cystic fibrosis transmembrane receptor, hexosaminidase A, hexosaminidase B, ß-galactosidase, and alpha-glucosidase.

In some embodiments, the compounds disclosed herein prevent and/or inhibit crystallin protein aggregation. In some embodiments, the compounds disclosed herein dissolve the lens crystallin protein aggregate(s) in the eye of the said subject. In some embodiments, the lens crystallin protein aggregate is α-crystallin, ß-crystallin, or γ-crystallin.

Diseases and Disorders

Disclosed herein are methods of treating a disease or disorder in a subject in need thereof, comprising administering a therapeutically effective amount of any one of the compounds disclosed herein. In some embodiments, the disease or disorder is an eye disease or disorder.

In some embodiments, the eye disease or disorder affects the normal structure of the lens in the eye. In some embodiments, the eye disease or disorder affects the structure of the lens as to cause vision dysfunction, such as changes to lens rigidity or clarity. Such eye diseases or disorders include but are not limited cataracts, congenital cataracts, cortical opacities, posterior subcapsular cataracts, presbyopia, nuclear sclerosis, retinal degenerative disorder, Refsum disease, Smith-Lemli-Opitz syndrome, Schnyder crystalline corneal dystrophy, drusen, age-related macular degeneration, abetalipoproteinemia, familial hypobetalipoproteinemia, and diabetic retinopathy. In some embodiments, the eye disease or disorder is cataracts, congenital cataracts, cortical opacities, posterior subcapsular cataracts, presbyopia, nuclear sclerosis, retinal degenerative disorder, Refsum disease, Smith-Lemli-Opitz syndrome, Schnyder crystalline corneal dystrophy, drusen, age-related macular degeneration, abetalipoproteinemia, familial hypobetalipoproteinemia, and diabetic retinopathy. In some embodiments, the eye disease or disorder is cataracts, congenital cataracts, cortical opacities, posterior subcapsular cataract, presbyopia, nuclear sclerosis, retinal degenerative disorder, Refsum disease, Smith-Lemli-Opitz syndrome, Schnyder crystalline corneal dystrophy, drusen, age-related macular degeneration, and diabetic retinopathy.

The term "cataract" as used herein refers to a disease or condition that causes cloudiness or opacity on the surface and/or inside of the lens. In some instances, cataract includes swelling of the lens. Examples of cataract include but are not limited to an age-related cataract, a diabetic cataract, a cataract associated with surgery, a cataract resulting from radiation exposure, a cataract resulting from an infection, a cataract resulting from medication, or a cataract resulting from a genetic illness.

Cataract includes both acquired cataract and congenital cataract. Examples of congenital cataract include but are not limited to congenital pseudo-cataract, congenital membrane cataract, congenital coronary cataract, congenital lamellar cataract, congenital punctuate cataract, and congenital filamentary cataract. Examples of acquired cataract include but are not limited to geriatric cataract, secondary cataract, browning cataract, complicated cataract, diabetic cataract, traumatic cataract, postoperative cataract, and cataracts resulting from electric shock, radiation, drugs, systemic diseases, and nutritional disorder.

In another aspect provided herein are methods of treating or preventing an eye disease or disorder in a subject in need thereof, comprising administering a therapeutically effective amount of any one of the compounds disclosed herein. In some embodiments, the subject is having or at risk of developing an eye disease or disorder that affects the normal structure of the lens in the eye. In some embodiments, the eye disease or disorder is selected from the group consisting of cataracts, congenital cataracts, cortical opacities, posterior subcapsular cataracts, presbyopia, nuclear sclerosis, retinal degenerative disorder, Refsum disease, Smith-Lemli-Opitz syndrome, Schnyder crystalline corneal dystrophy, drusen, age-related macular degeneration, and diabetic retinopathy. In some embodiments, the compound inhibits crystallin protein aggregation.

In another aspect provided herein are methods of treating cataract or blindness/impaired vision in a subject in need thereof comprising administering a therapeutically effective amount of any one of the compounds disclosed herein. In some embodiments, the compound dissolves the lens crystallin protein aggregate(s) in the eye of the subject. In some embodiments, the lens crystallin protein aggregate is α-crystallin, β-crystallin, or γ-crystallin.

Compounds

Disclosed herein are tetracyclic compounds or steroid derivatives. In some embodiments, these compounds are sterol derivatives. In one aspect, disclosed herein is a compound of Formula (Ic):

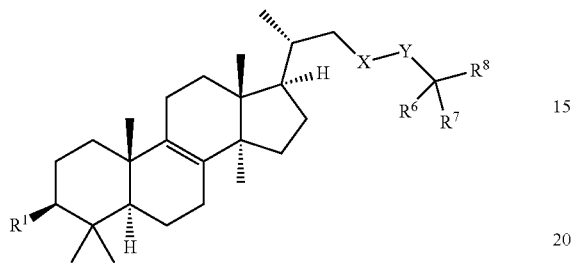

Formula (Ic)

or a pharmaceutically acceptable salt thereof,
wherein
X is —C(R$^4$)$_2$—;
each R$^4$ is independently hydrogen, —OR$^e$, optionally substituted C$_1$-C$_6$alkyl, or halogen;
each R$^e$ is independently hydrogen, optionally substituted C$_1$-C$_6$alkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;
Y is —C(R$^5$)$_2$—;
each R$^5$ is independently hydrogen, —OR$^g$, optionally substituted C$_1$-C$_6$alkyl, or halogen;
R$^g$ is independently hydrogen, optionally substituted C$_1$-C$_6$alkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;
each R$^6$, R$^7$, and R$^8$ is independently hydrogen, optionally substituted C$_1$-C$_6$alkyl, halogen, —OR$^h$, —SR$^h$, or —N(R$^i$)$_2$;
each R$^h$ is independently hydrogen, optionally substituted C$_1$-C$_6$alkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;
each R$^i$ is independently hydrogen, optionally substituted C$_1$-C$_6$alkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two R$^i$ are taken together with the N atom to which they are attached to form an optionally substituted heterocycloalkyl ring;
R$^1$ is —OR$^{10}$, —SR$^{10}$, —N(R$^{10}$)$_2$, or halogen; and
each R$^{10}$ is independently hydrogen, optionally substituted C$_1$-C$_6$alkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or
two R$^{10}$ are taken together with the N atom to which they are attached to form an optionally substituted heterocycloalkyl ring.

In some embodiments, X is —CH$_2$— or —CH(OR$^e$)—. In some embodiments, R$^e$ is hydrogen. In some embodiments, Y is —CH$_2$—, —CH(OR$^g$)—, or —CH(R$^5$)—; and wherein R$^5$ is optionally substituted C$_1$-C$_6$alkyl or halogen. In some embodiments, R$^g$ is hydrogen. In some embodiments, R$^5$ is —Br or —F. In some embodiments, R$^5$ is methyl or ethyl. In some embodiments, R$^6$ and R$^7$ are each independently C$_1$-C$_3$ alkyl. In some embodiments, R$^6$ and R$^7$ are each independently methyl. In some embodiments, R$^8$ is hydrogen, —OR$^h$, or —N(R$^i$)$_2$.

In some embodiments, the compound disclosed herein, or the pharmaceutically acceptable salt thereof, has a Formula (Id):

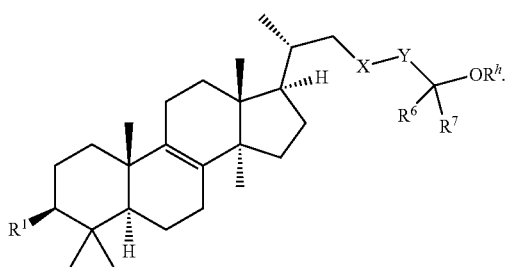

Formula (Id)

In some embodiments, R$^h$ is hydrogen.

In some embodiments, the compound disclosed herein is selected from:

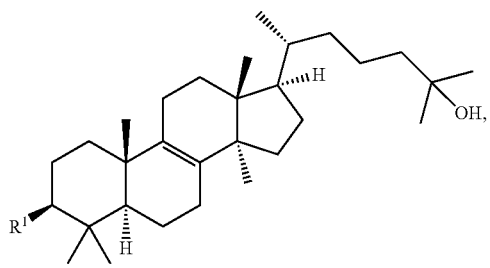

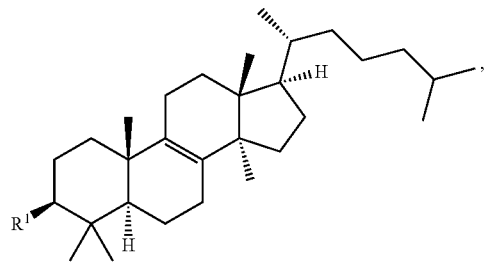

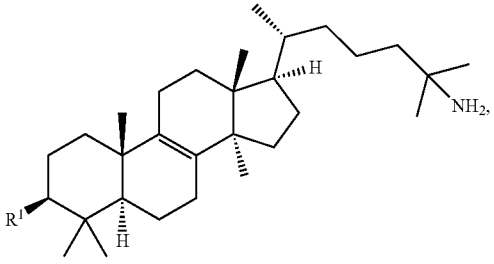

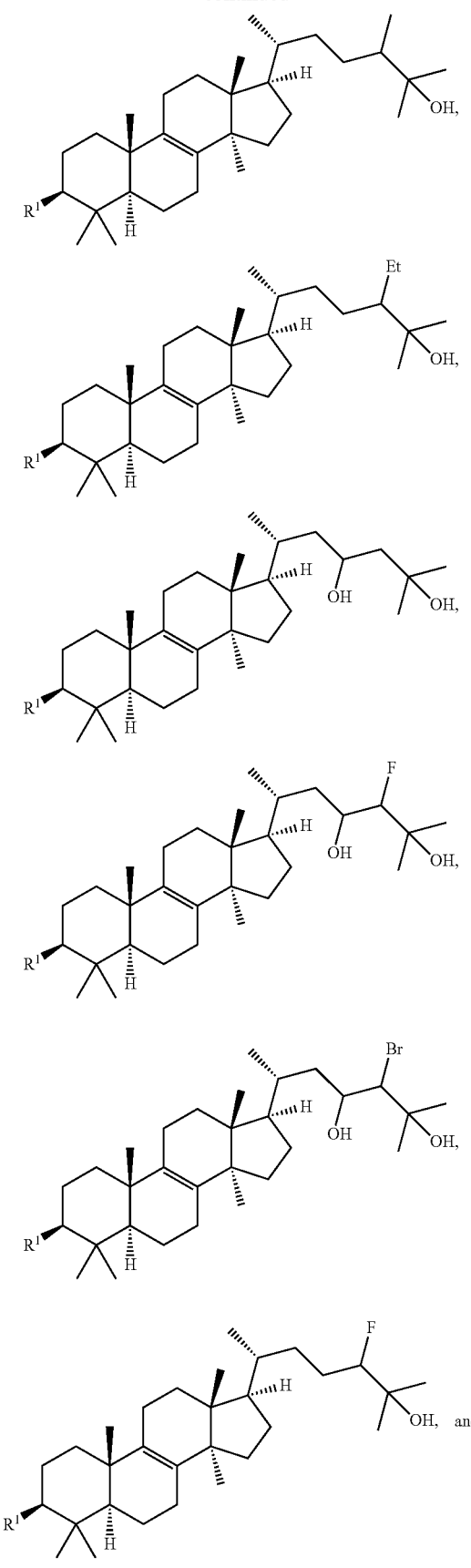

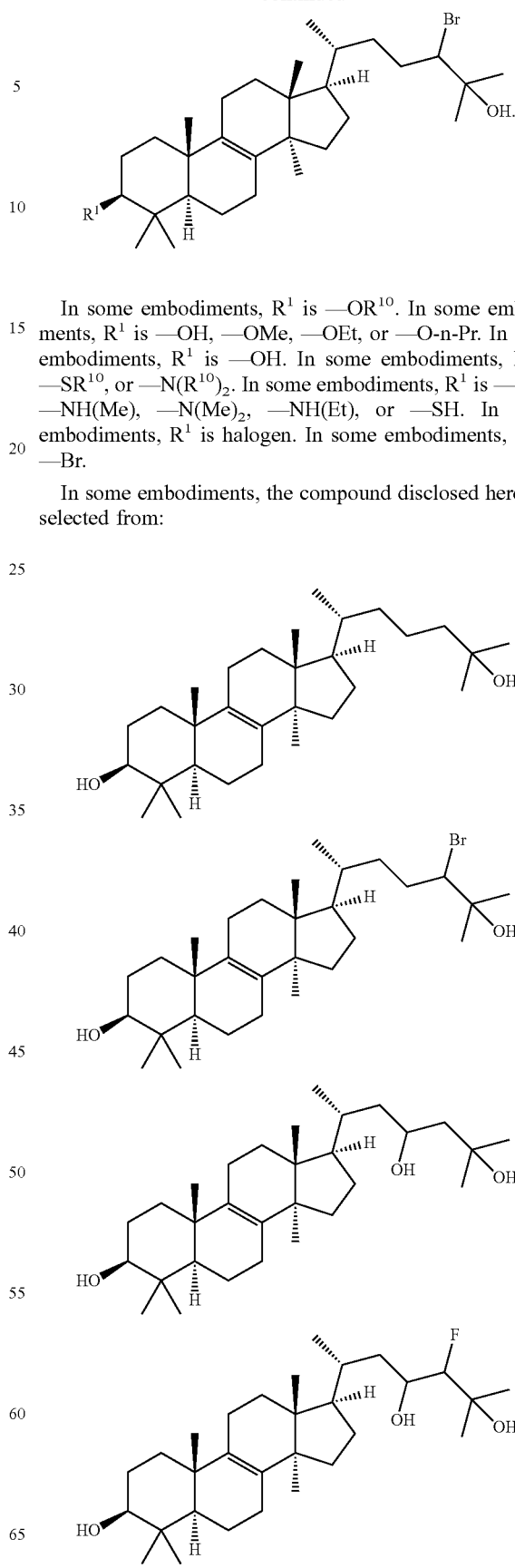

In some embodiments, $R^1$ is $-OR^{10}$. In some embodiments, $R^1$ is $-OH$, $-OMe$, $-OEt$, or $-O$-$n$-Pr. In some embodiments, $R^1$ is $-OH$. In some embodiments, $R^1$ is $-SR^{10}$, or $-N(R^{10})_2$. In some embodiments, $R^1$ is $-NH_2$, $-NH(Me)$, $-N(Me)_2$, $-NH(Et)$, or $-SH$. In some embodiments, $R^1$ is halogen. In some embodiments, $R^1$ is $-Br$.

In some embodiments, the compound disclosed herein is selected from:

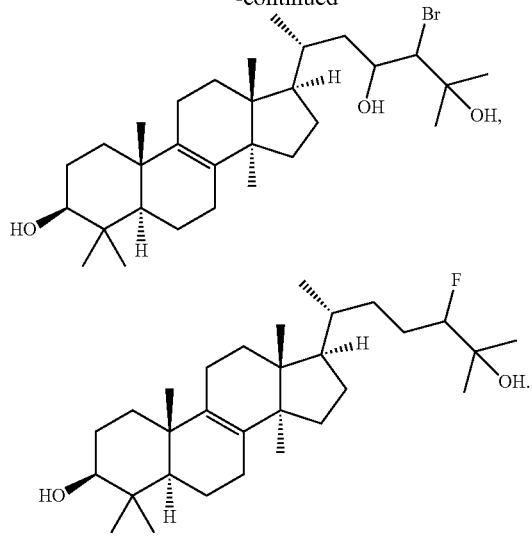

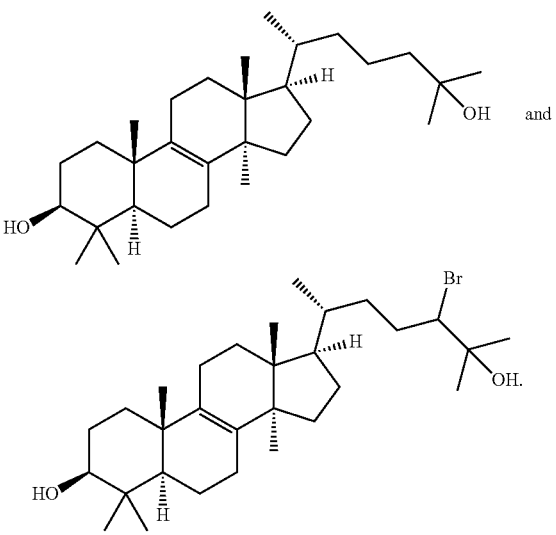

In some embodiments, the compound disclosed herein is selected from:

In some embodiments, the compounds of Formula (I) are any one of the compounds disclosed in Tables 1-3.

TABLE 1

| Chemical Synthesis Example | Structure | Name |
|---|---|---|
| 2 | 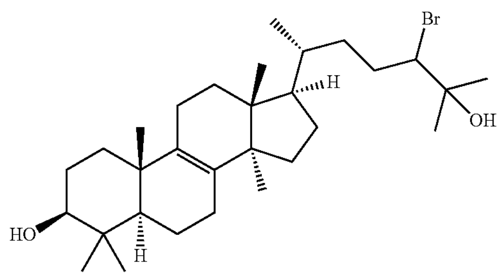 [SMILES: C[C@H](CCC(Br)C(C)(C)O)[C@H]1CC[C@@]2(C)C3=C(CC[C@]12C)[C@@]1(C)CC[C@H](O)C(C)(C)[C@@H]1CC3] | (3S,5R,10S,13R,14R,17R)-17-((2R)-5-bromo-6-hydroxy-6-methylheptan-2-yl)-4,4,10,13,14-pentamethyl-2,3,4,5,6,7,10,11,12,13,14,15,16,17-tetradecahydro-1H-cyclopenta[a]phenanthren-3-ol |
| 1 | 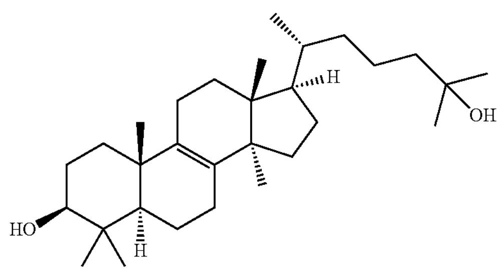 [SMILES: C[C@H](CCCC(C)(C)O)[C@H]1CC[C@@]2(C)C3=C(CC[C@]12C)[C@@]1(C)CC[C@H](O)C(C)(C)[C@@H]1CC3] | (3S,5R,10S,13R,14R,17R)-17-((R)-6-hydroxy-6-methylheptan-2-yl)-4,4,10,13,14-pentamethyl-2,3,4,5,6,7,10,11,12,13,14,15,16,17-tetradecahydro-1H-cyclopenta[a]phenanthren-3-ol |

TABLE 2

| Structure | Name |
|---|---|
| 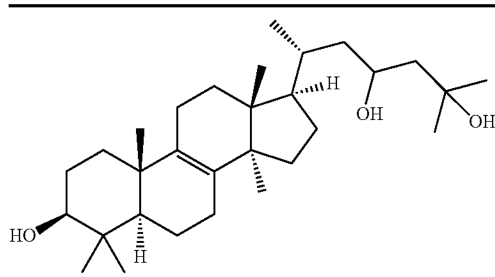 | (6R)-6-((3S,5R,10S,13R,14R,17R)-3-hydroxy-4,4,10,13,14-pentamethyl-2,3,4,5,6,7,10,11,12,13,14,15,16,17-tetradecahydro-1H-cyclopenta[a]phenanthren-17-yl)-2-methylheptane-2,4-diol |

TABLE 2-continued

| Structure | Name |
|---|---|
| [structure] | (6R)-3-fluoro-6-((3S,5R,10S,13R,14R,17R)-3-hydroxy-4,4,10,13,14-pentamethyl-2,3,4,5,6,7,10,11,12,13,14,15,16,17-tetradecahydro-1H-cyclopenta[a]phenanthren-17-yl)-2-methylheptane-2,4-diol |
| [structure] | (6R)-3-bromo-6-((3S,5R,10S,13R,14R,17R)-3-hydroxy-4,4,10,13,14-pentamethyl-2,3,4,5,6,7,10,11,12,13,14,15,16,17-tetradecahydro-1H-cyclopenta[a]phenanthren-17-yl)-2-methylheptane-2,4-diol |
| [structure] | (3S,5R,10S,13R,14R,17R)-17-((2R)-5-fluoro-6-hydroxy-6-methylheptan-2-yl)-4,4,10,13,14-pentamethyl-2,3,4,5,6,7,10,11,12,13,14,15,16,17-tetradecahydro-1H-cyclopenta[a]phenanthren-3-ol |

TABLE 3

TABLE 3-continued

TABLE 3-continued

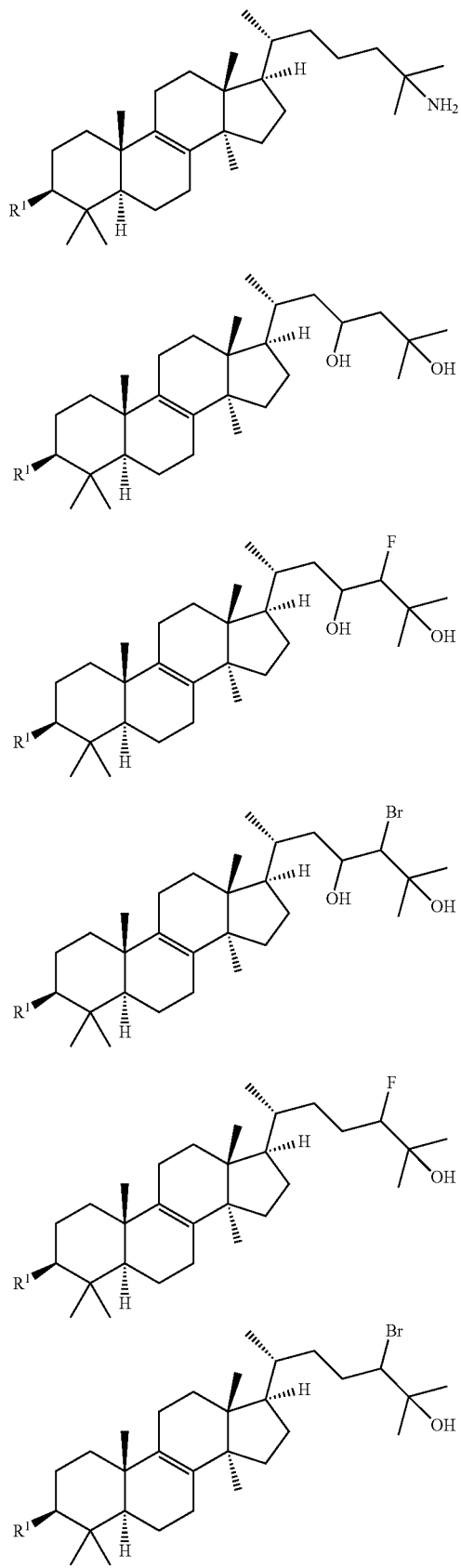

In some embodiments, $R^1$ is —$OR^{10}$, —$N(R^{10})_2$, —$SR^{10}$, or halogen in Table 3. In some embodiments, $R^1$ is —OH, —OMe, —OEt, —O-n-Pr, —$NH_2$, —NH(Me), —$N(Me)_2$, —NH(Et), —SH, or —Br in Table 3.

Any combination of the groups described above for the various variables is contemplated herein. Throughout the specification, groups and substituents thereof are chosen by one skilled in the field to provide stable moieties and compounds.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the disclosure include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvates, hydrates, or derivatives thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically acceptable salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, or inorganic or organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three or four) amino acid residues is covalently joined through an amide or ester bond to a free amino, hydroxy, or carboxylic acid group of compounds of the present disclosure. The amino acid residues include but are not limited to the 20 naturally occurring amino acids and also include 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including but not limited to ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to, the following groups and combinations of groups:

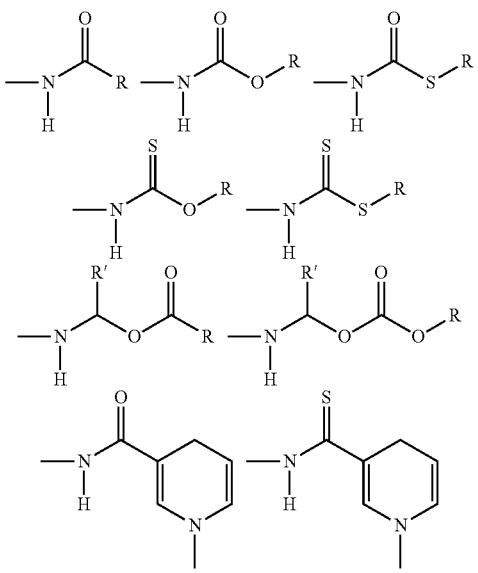

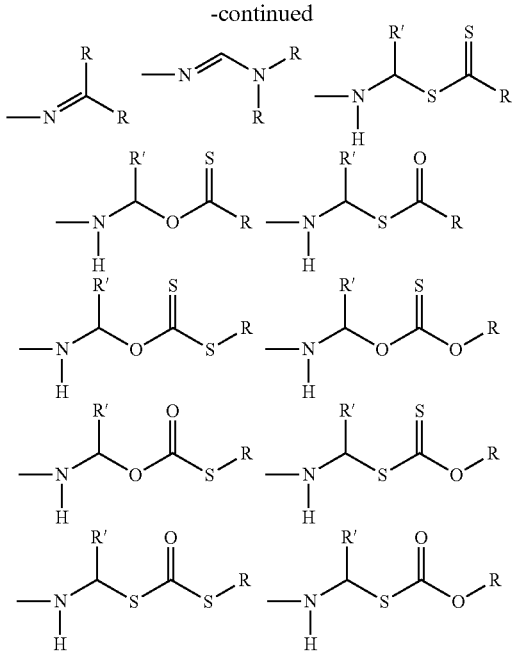

as well as sulfonamides and phosphonamides.

In certain instances, sites on any aromatic ring portions are susceptible to various metabolic reactions, therefore incorporation of appropriate substituents on the aromatic ring structures, reduce, minimize, or eliminate this metabolic pathway in some embodiments.

Metabolites

In some embodiments, the compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen or an alkyl group.

In additional or further embodiments, the compounds described herein are metabolized upon administration to an organism in need to produce a metabolite that is then used to produce a desired effect, including a desired therapeutic effect.

Synthesis of Compounds

The compounds of described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6$^{th}$ Edition, John Wiley and Sons, Inc. In some instances, alternative reaction conditions for the synthetic transformations described herein are employed such as variation of solvent, reaction temperature, reaction time, as well as different chemical reagents and other reaction conditions. The starting materials are available from commercial sources or are readily prepared.

Suitable reference books and treatises that detail the synthesis of reactants useful in the preparation of compounds described herein, or provide references to articles that describe the preparation, include, for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some embodiments, the compounds described herein are prepared by the general synthetic route described below in Schemes 1-3.

In some embodiments, the compounds disclosed herein, such as Compound 1, are prepared through the synthetic route as shown in Scheme 1. In some instances, Compound I-1 is brominated with a suitable bromination agent, such as bromine or NBS, to provide Compound I-2.

Scheme 1

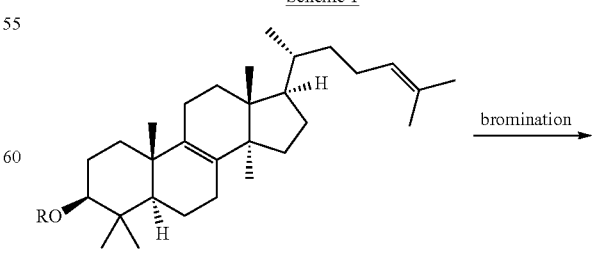

R = TBS, Tr, Ac, etc.

I-1

33
-continued

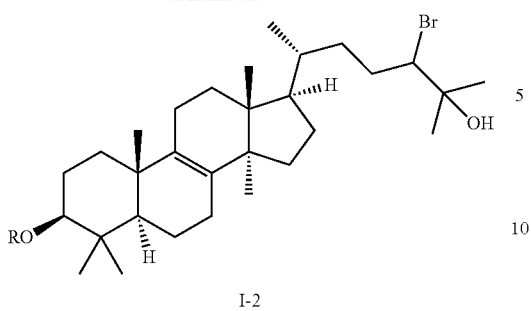

I-2

34
-continued

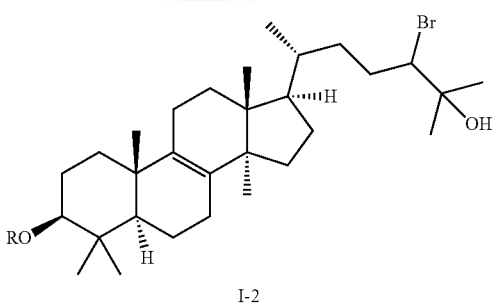

I-2

R = TBS, Tr, Ac, etc.

Alternatively, the compounds disclosed herein, such as Compound 1, are prepared through the synthetic route as shown in Scheme 2. In some embodiments, Compound I-1 is subjected under suitable dihydroxylation conditions with an appropriate reagent to provide Compound II-2. In some embodiments, Compound II-2 is subjected under appropriate conditions to provide Compound II-3. In some instances, Compound II-3 is treated with suitable reagents and reaction conditions to provide Compound I-2.

In some embodiments, the compounds disclosed herein, such as Compound 2, are prepared through the synthetic route as shown in Scheme 3. In some instances, Compound III-1 is subjected under suitable conditions to provide Compound I-1. In some embodiments, Compound I-1 is then subjected under appropriate oxidation conditions to provide Compound III-2. In some embodiments, Compound III-2 is then subjected under appropriate reaction conditions to provide Compound III-3.

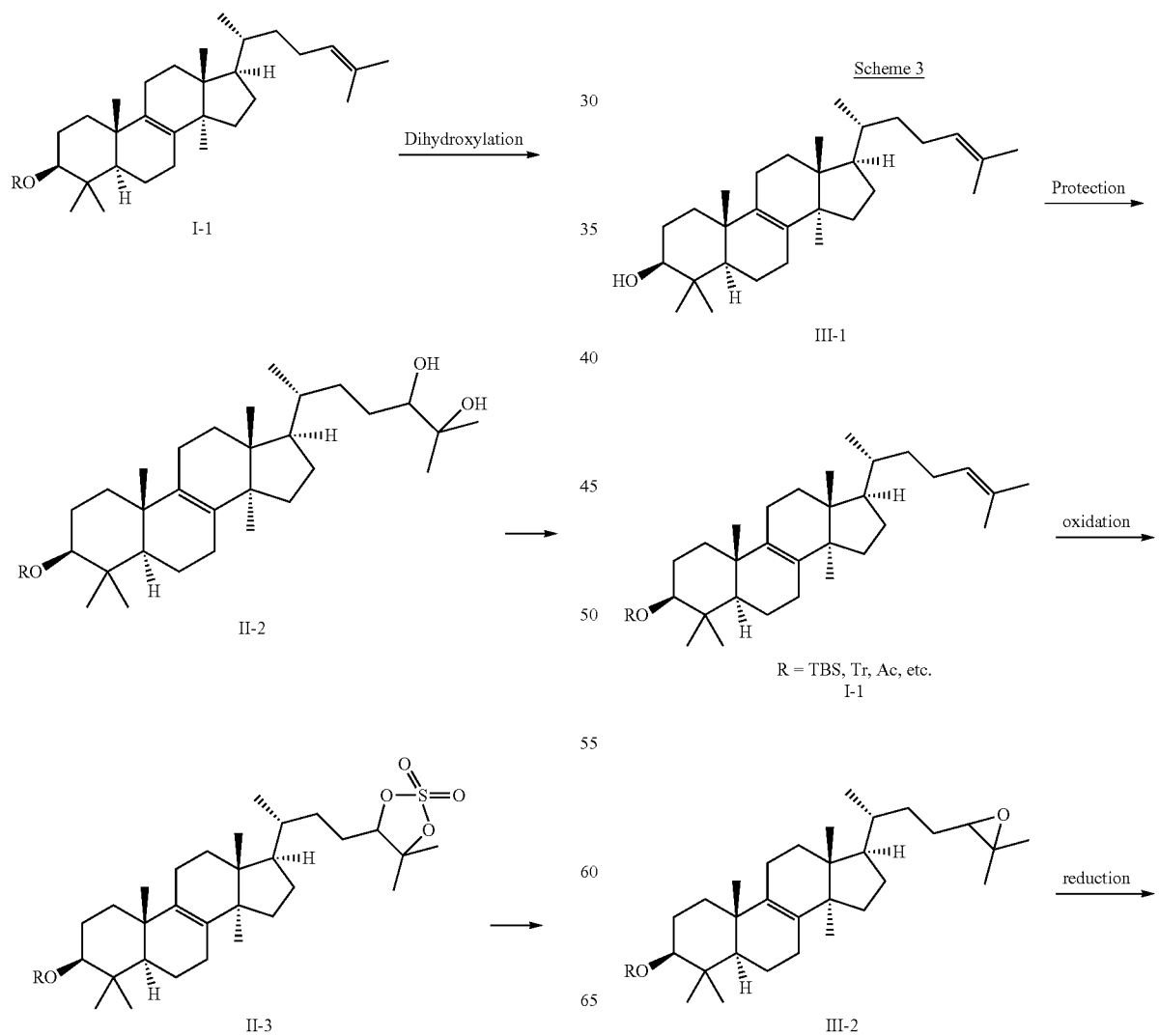

-continued

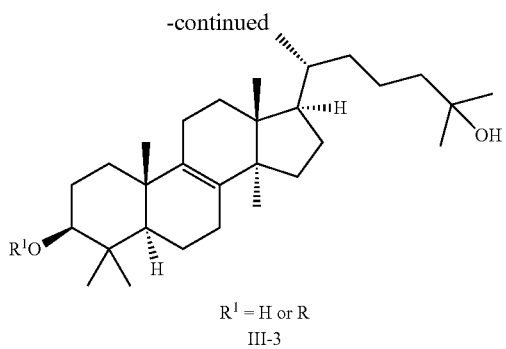

R¹ = H or R
III-3

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999). In some embodiments, the compounds described herein are administered either alone or in combination with pharmaceutically acceptable carriers, excipients or diluents, in a pharmaceutical composition.

Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route, in some instances, depends upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. In some embodiments, tablets are made by compression or molding, optionally with one or more accessory ingredients. In some embodiments, compressed tablets are prepared by compressing in a suitable machine the active ingredient in a free-flowing form such as a powder or granules, optionally mixed with binders, inert diluents, or lubricating, surface active or dispersing agents. In some instances, molded tablets are made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In some embodiments for soft capsules, the active compounds are dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions are used in some embodiments, which optionally contain gum arabic, talc, polyvinyl pyrrolidone, carbopol gel, polyethylene glycol, and/or titanium dioxide, lacquer solutions, and suitable organic solvents or solvent mixtures. In some embodiments, dyestuffs or pigments are added to the tablets or Dragee coatings for identification or to characterize different combinations of active compound doses.

In some embodiments, pharmaceutical compositions are formulated for parenteral administration by injection, e.g., by bolus injection or continuous infusion. In some embodiments, formulations for injection are presented in unit dosage form, e.g., in ampoules or in multi-dose containers, with an added preservative. In some embodiments, the compositions take such forms as suspensions, solutions or emulsions in oily or aqueous vehicles, and optionally contain formulatory agents such as suspending, stabilizing and/or dispersing agents. In some embodiments, the compositions are presented in unit-dose or multi-dose containers, for example sealed ampoules and vials, and are optionally stored in powder form or in a freeze-dried (lyophilized) condition requiring only the addition of the sterile liquid carrier, for example, saline or sterile pyrogen-free water, immediately prior to use. Extemporaneous injection solutions and suspensions are optionally prepared from sterile powders, granules and tablets of the kind previously described.

Pharmaceutical compositions for parenteral administration include aqueous and non-aqueous (oily) sterile injection solutions of the active compounds which optionally contain antioxidants, buffers, bacteriostats and solutes which render the formulation isotonic with the blood of the intended recipient; and aqueous and non-aqueous sterile suspensions which optionally include suspending agents and thickening agents. Suitable lipophilic solvents or vehicles include fatty oils such as sesame oil, or synthetic fatty acid esters, such as ethyl oleate or triglycerides, or liposomes. In some embodiments, aqueous injection suspensions contain substances which increase the viscosity of the suspension, such as sodium carboxymethyl cellulose, sorbitol, or dextran. Optionally, the suspension also contains suitable stabilizers or agents which increase the solubility of the compounds to allow for the preparation of highly concentrated solutions.

In some embodiments, pharmaceutical compositions are also formulated as a depot preparation. Such long acting formulations are administered by implantation (for example subcutaneously or intramuscularly) or by intramuscular injection in some embodiments. Thus, for example, the compounds are formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions take the form of tablets, lozenges, pastilles, or gels formulated in conventional manner in some embodiments. Such compositions optionally comprise the active ingredient in a flavored basis such as sucrose and acacia or tragacanth.

In some embodiments, pharmaceutical compositions are also formulated in rectal compositions such as suppositories or retention enemas, e.g., containing conventional suppository bases such as cocoa butter, polyethylene glycol, or other glycerides.

In some embodiments, pharmaceutical compositions are administered topically, that is by non-systemic administration. This includes the application of a compound of the present disclosure externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. In some embodiments, the active ingredient comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. In some embodiments, pressurized packs comprise a suitable propellant such as dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount in some embodiments. Alternatively, for administration by inhalation or insufflation, pharmaceutical preparations take the form of a dry powder composition in some instances, for example a powder mix of the compound and a suitable powder base such as lactose or starch. In some embodiments, the powder composition is presented in unit dosage form, in for example, capsules, cartridges, gelatin or blister packs from which the powder is administered with the aid of an inhalator or insufflator in some instances.

It should be understood that in addition to the ingredients particularly mentioned above, the compounds and compositions described herein, in some instances, include other agents conventional in the art having regard to the type of formulation in question, for example those suitable for oral administration include flavoring agents in some embodiments.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e. a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

EXAMPLES

The following examples are provided for illustrative purposes only and not to limit the scope of the claims provided herein.

Example 1

(3S,5R,10S,13R,14R,17R)-17-((R)-6-hydroxy-6-methylheptan-2-yl)-4,4,10,13,14-pentamethyl-2,3,4,5,6,7,10,11,12,13,14,15,16,17-tetradecahydro-1H-cyclopenta[a]phenanthren-3-ol (Compound 2)

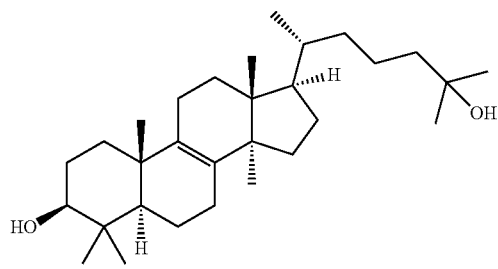 [SMILES: C[C@H](CCCC(C)(C)O)[C@H]1CC[C@@]2(C)C3=C(CC[C@]12C)[C@@]1(C)CC[C@H](O)C(C)(C)[C@@H]1CC3]

The synthetic sequence for Compound 2 is illustrated in Scheme 4 below. It consists of four chemical steps and two prep-LC purifications. Using this sequence, 10 g Compound 2 has been prepared at >98% purity.

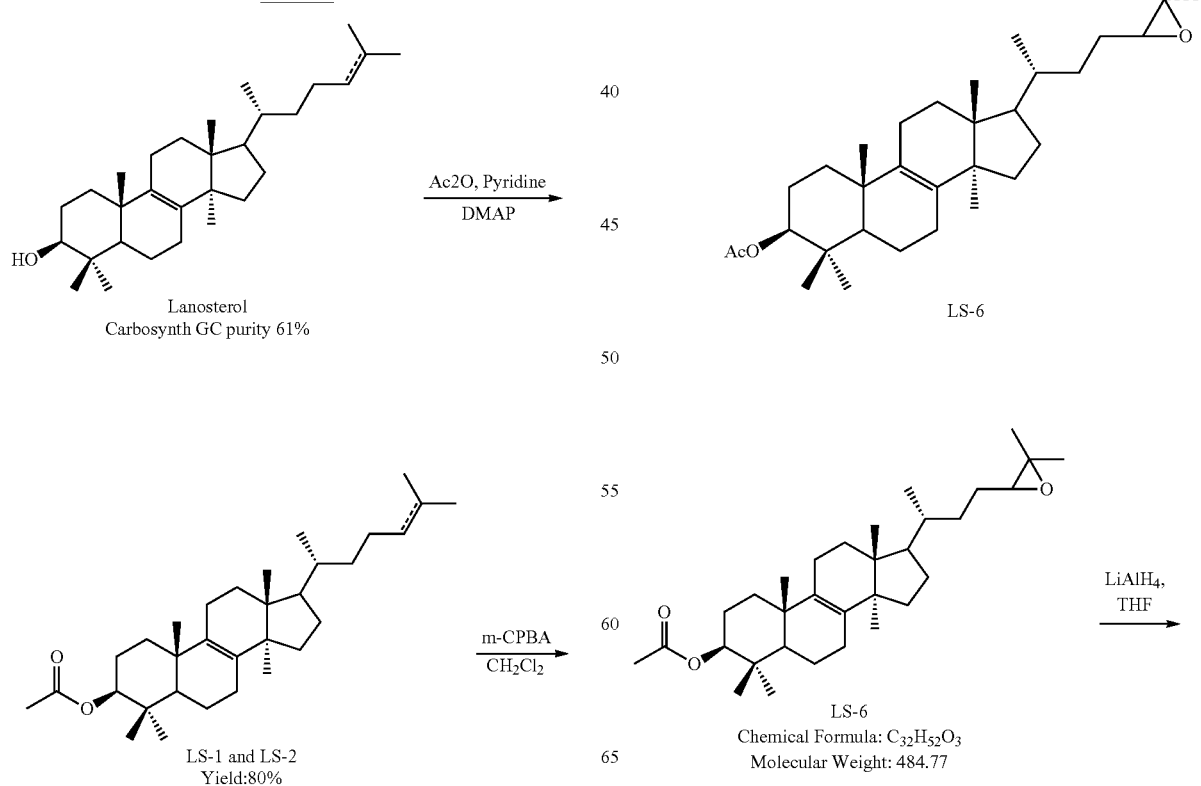

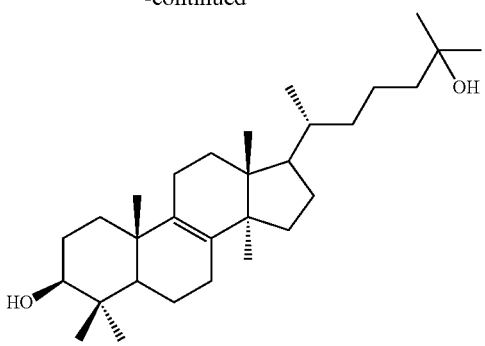

Compound 2
Chemical Formula: $C_{30}H_{52}O_2$
Molecular Weight: 444.73

Step 1: Purification of Commercial Lanosterol

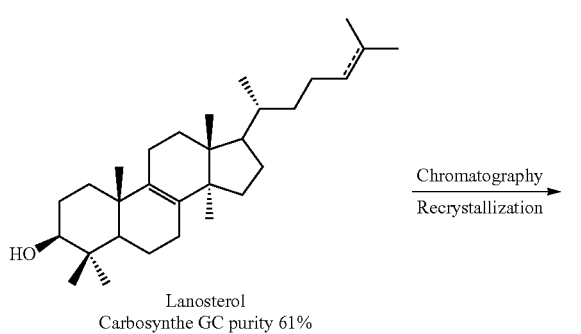

Lanosterol
Carbosynthe GC purity 61%

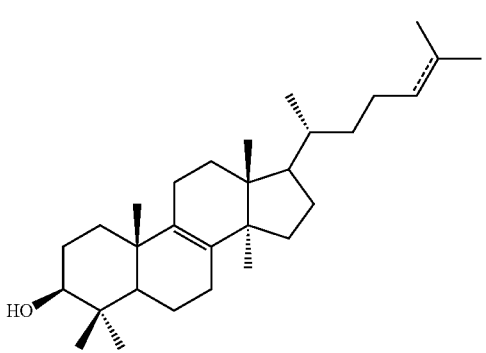

50 g commercial lanosterol (Carbosynth, Lot#FL71051) was purified on silica gel column using 200-300 mesh silica and Petroleum Ether:EtOAc=1:10 as eluent. The major component by TLC analysis was collected and concentrated to dryness. A further MeOH recrystallization of this material yielded the purified lanosterol (43 g; 86% yield).

Commercially available lanosterol from different sources varied in quality. Commercially available lanosterol from TCI and Carbosynth had different purities but the main common impurity was dihydro-lanosterol, which is structurally very similar to lanosterol. Various attempts to separate this impurity from lanosterol at this stage were unsuccessful, and it was concluded that the impurity or its subsequent derivative could be removed in the later stages.

Step 2: Preparation of LS-1 and LS-2

Figure 1B:
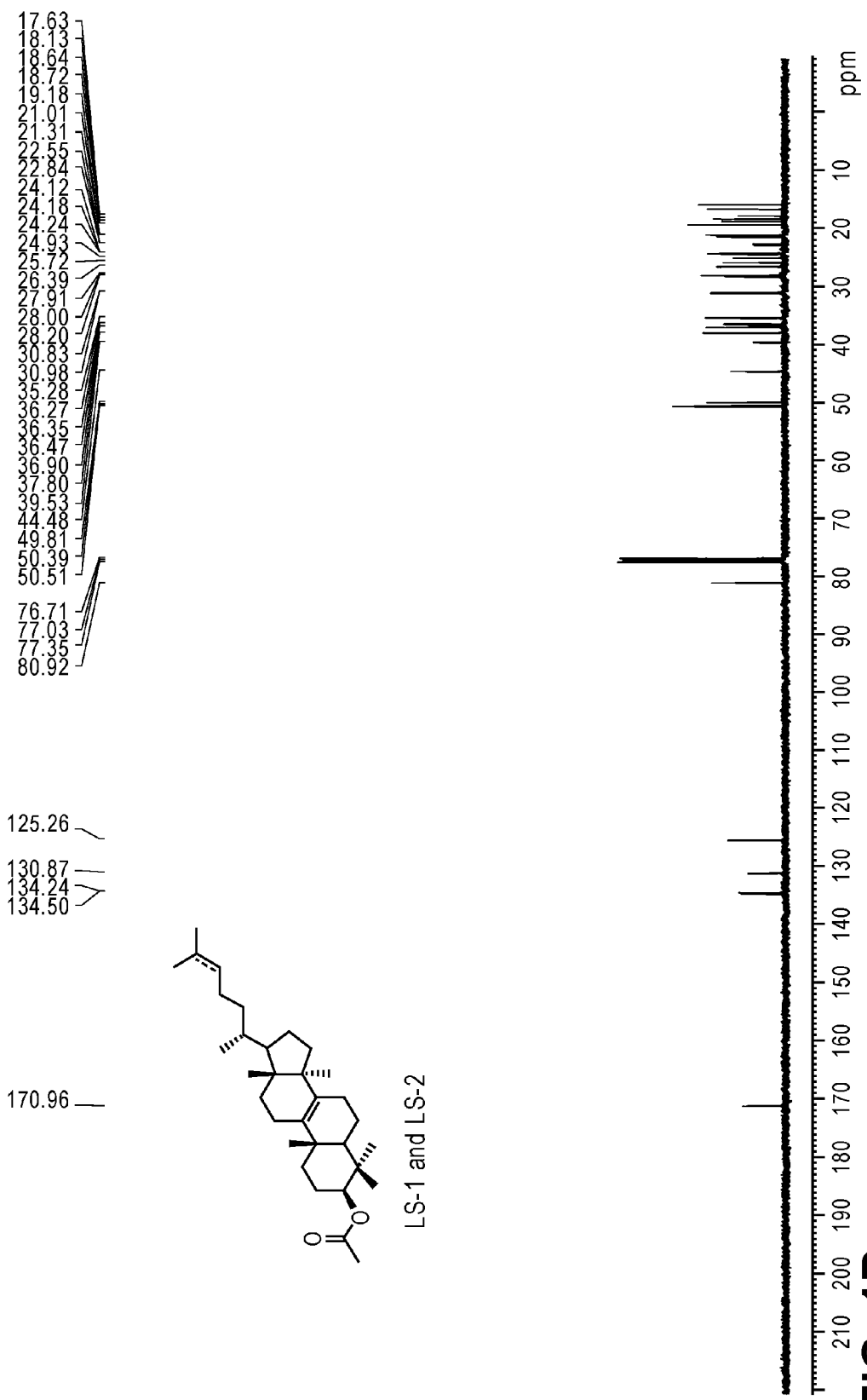

Lanosterol obtained from above purification with a GC purity of 61% (40 g, 93 mmol) was dissolved in 260 mL n-hexane. After the lanosterol had dissolved, acetic anhydride (18.4 mL, 186 mmol) and DMAP (18.2 g, 148.8 mmol) were added at 0° C. The reaction mixture was gradually warmed to room temperature and maintained at rt for 3 h. TLC showed completion of reaction. The reaction mixture was washed with water (250 mL), 5% HCl aqueous (250 mL), and saturated $NaHCO_3$ (250 mL). Anhydrous sodium sulfate was then added to dry the solution. The organic solution was concentrated to dryness to yield the crude product. The crude product was further recrystallized with methanol to yield a mixture of LS-1 and LS-2 (36.8 g, 85% yield). FIG. 1A shows the $^1H$ NMR of the mixture of LS-1 and LS-2 while FIG. 1B shows the $^{13}C$ NMR of the mixture of the LS-1 and LS-2.

Step 3: Preparation of LS-6 and LS-2 m-CPBA (10.41 g, 60.4 mmol, purity 70%) and $NaHCO_3$ (solid, 7.90 g, 94.1 mmol) were mixed well. The LS-1 and LS-2 mixture obtained from the last step (41.60 g, 88.8 mmol) was dissolved in 500 mL $CH_2Cl_2$. At 0° C., the above mixture of $NaHCO_3$ and m-CPBA was added in five batches. Temperature was kept at 0° C. and maintained for 2 h. The reaction mixture was filtered to remove the solid residue. The organic filtrate was washed sequentially with 10% $NaHCO_3$ aqueous solution (4×250 mL) and brine (250 mL). The organic solution was dried with $MgSO_4$ and evaporated under reduced pressure to provide the crude LS-6 and LS-2.

Step 4: Purification and Separation of LS-6 and LS-2

Figure 2A:
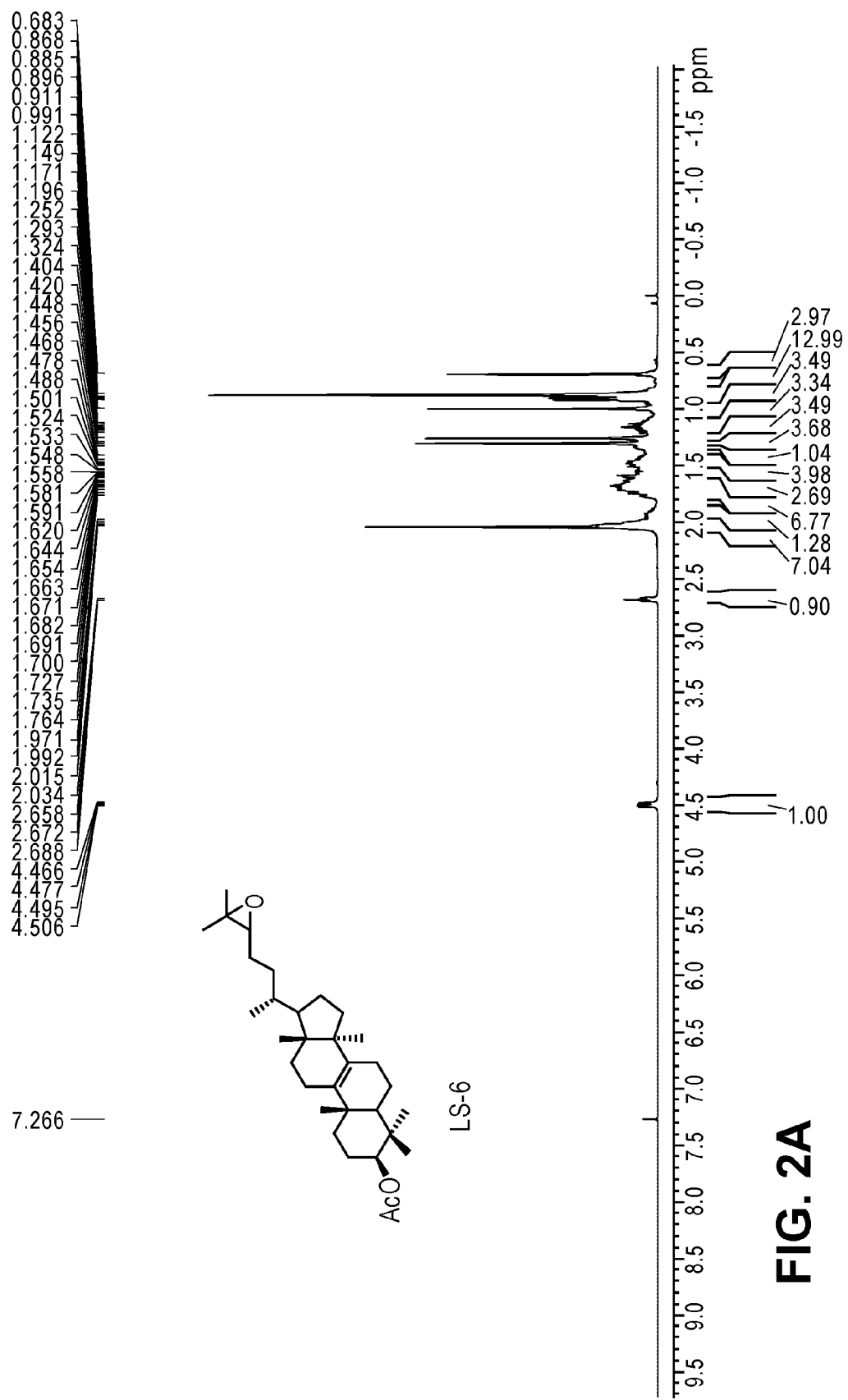
FIGS. 2A and 2B show the NMR data of LS-6.
Figure 2B:
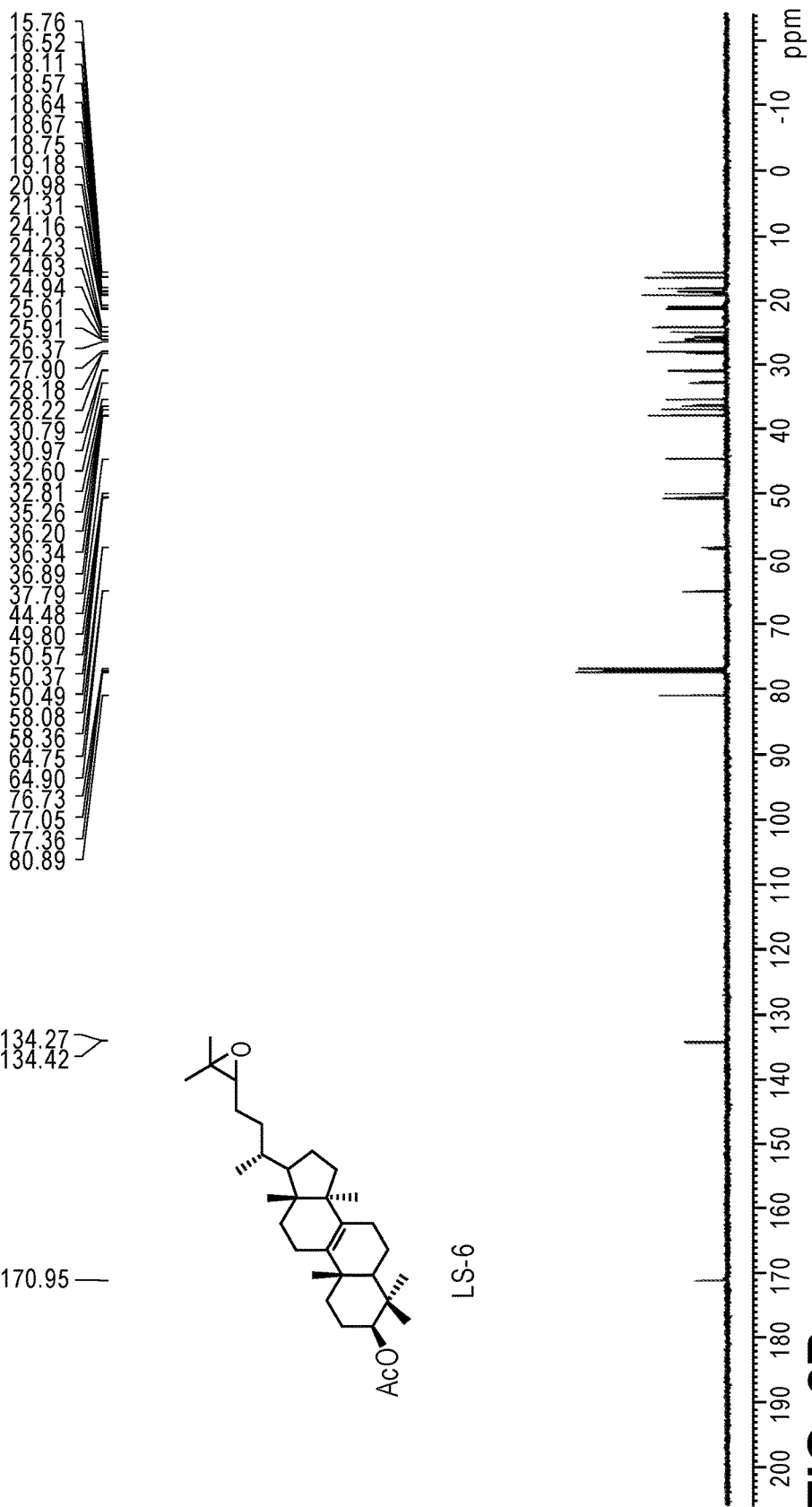
Figure 3A:
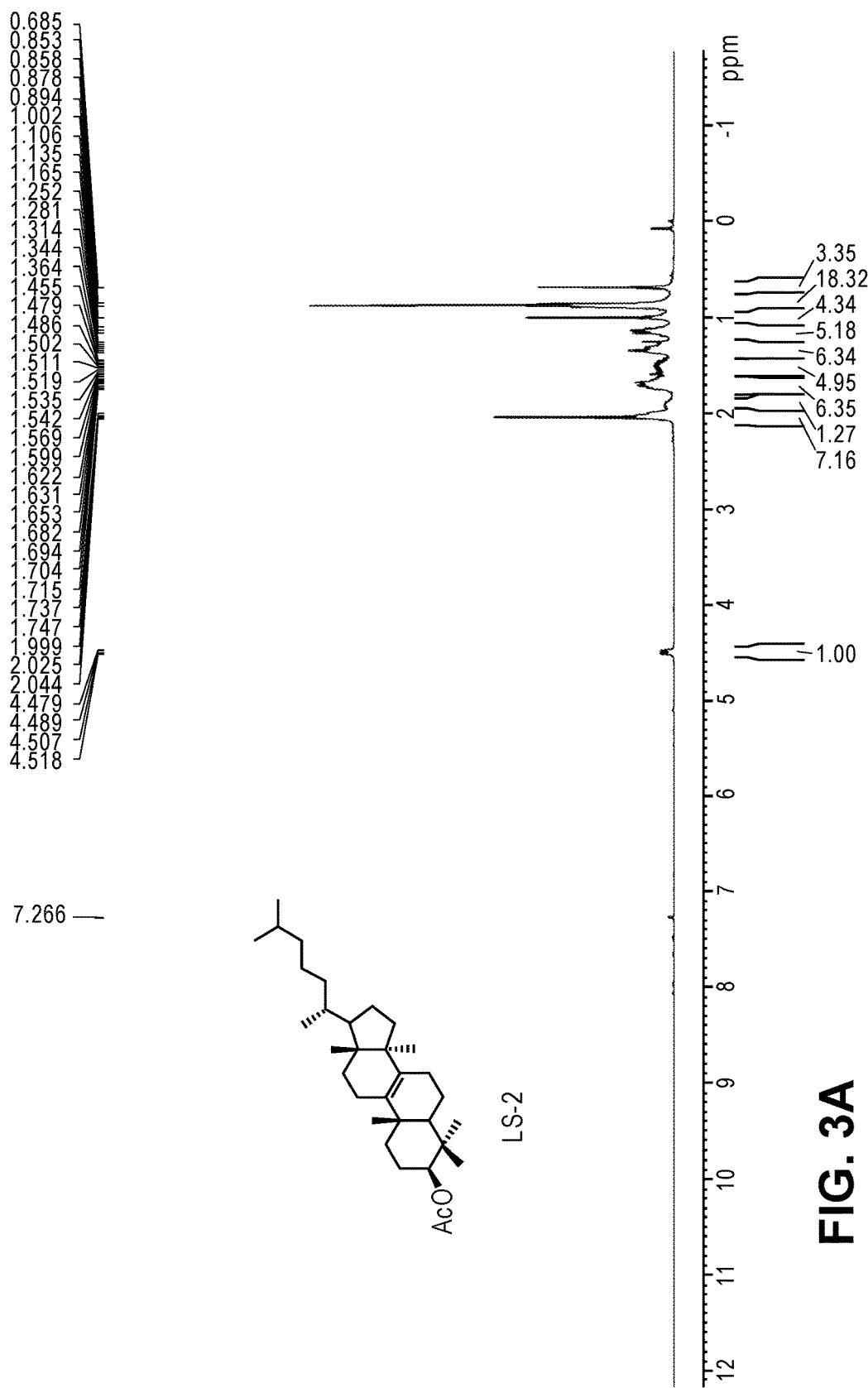
FIGS. 3A and 3B show the NMR data of LS-2.
Figure 3B:
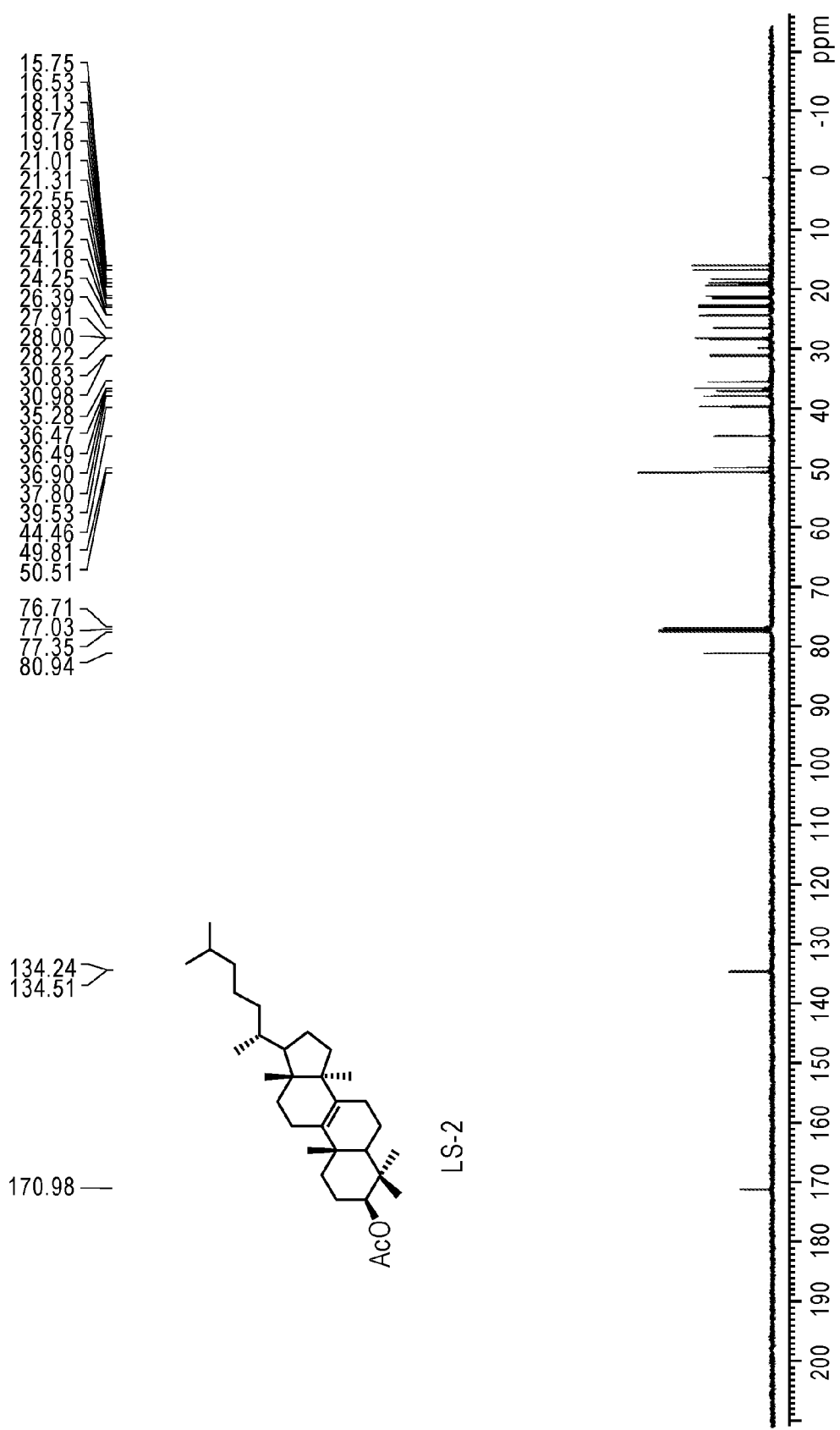

Prep-HPLC was used for the separation and purification of LS-6 and LS-2. FIG. 2A shows the $^1H$ NMR of LS-6 while FIG. 2B shows the $^{13}C$ NMR of LS-6. FIG. 3A shows the $^1H$ NMR of LS-2 while FIG. 3B shows the $^{13}C$ NMR of LS-2.

Step 5: Preparation of Compound 2

Figure 4A:
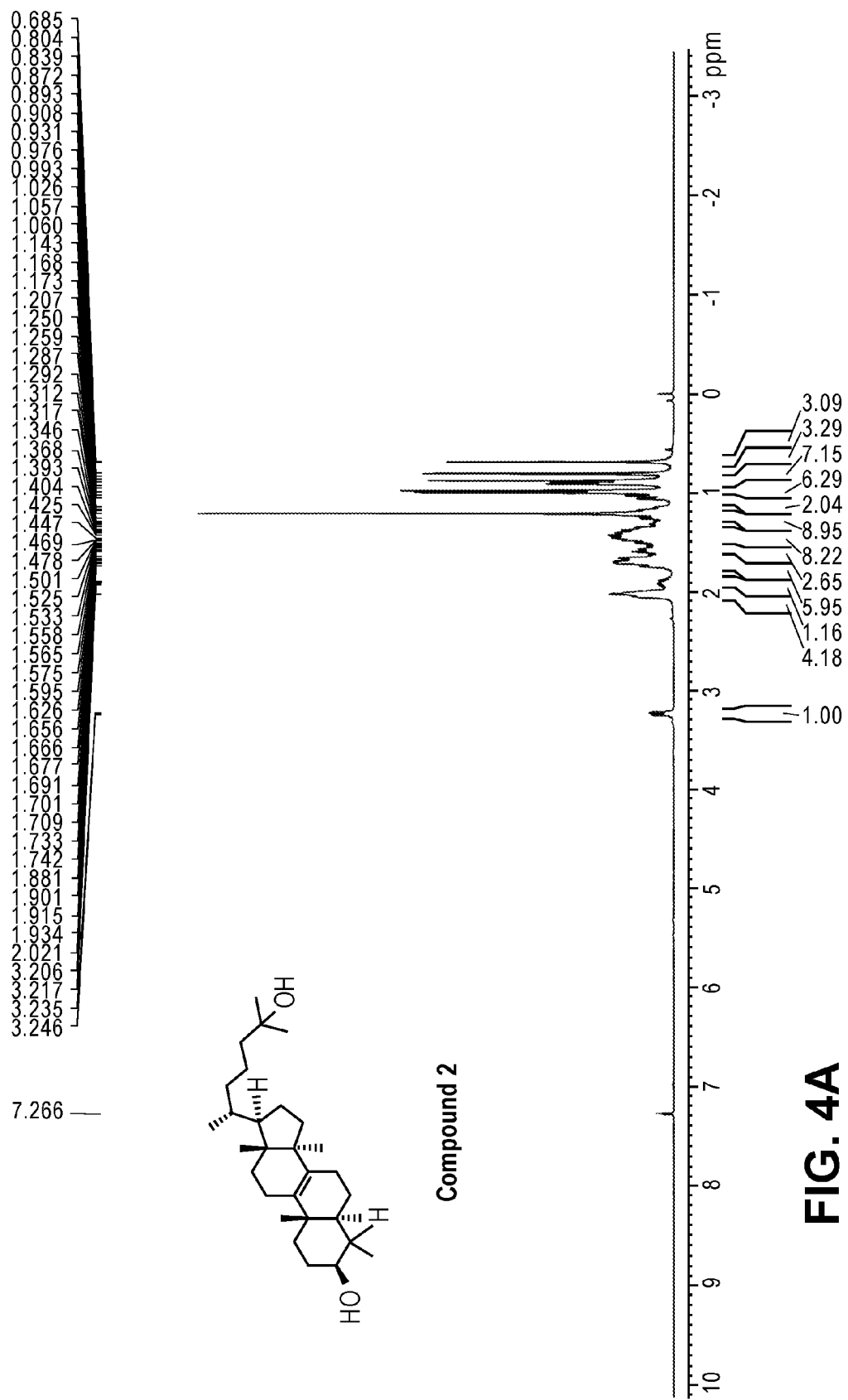
FIGS. 4A and 4B show the NMR data of Compound 2.
Figure 4B:
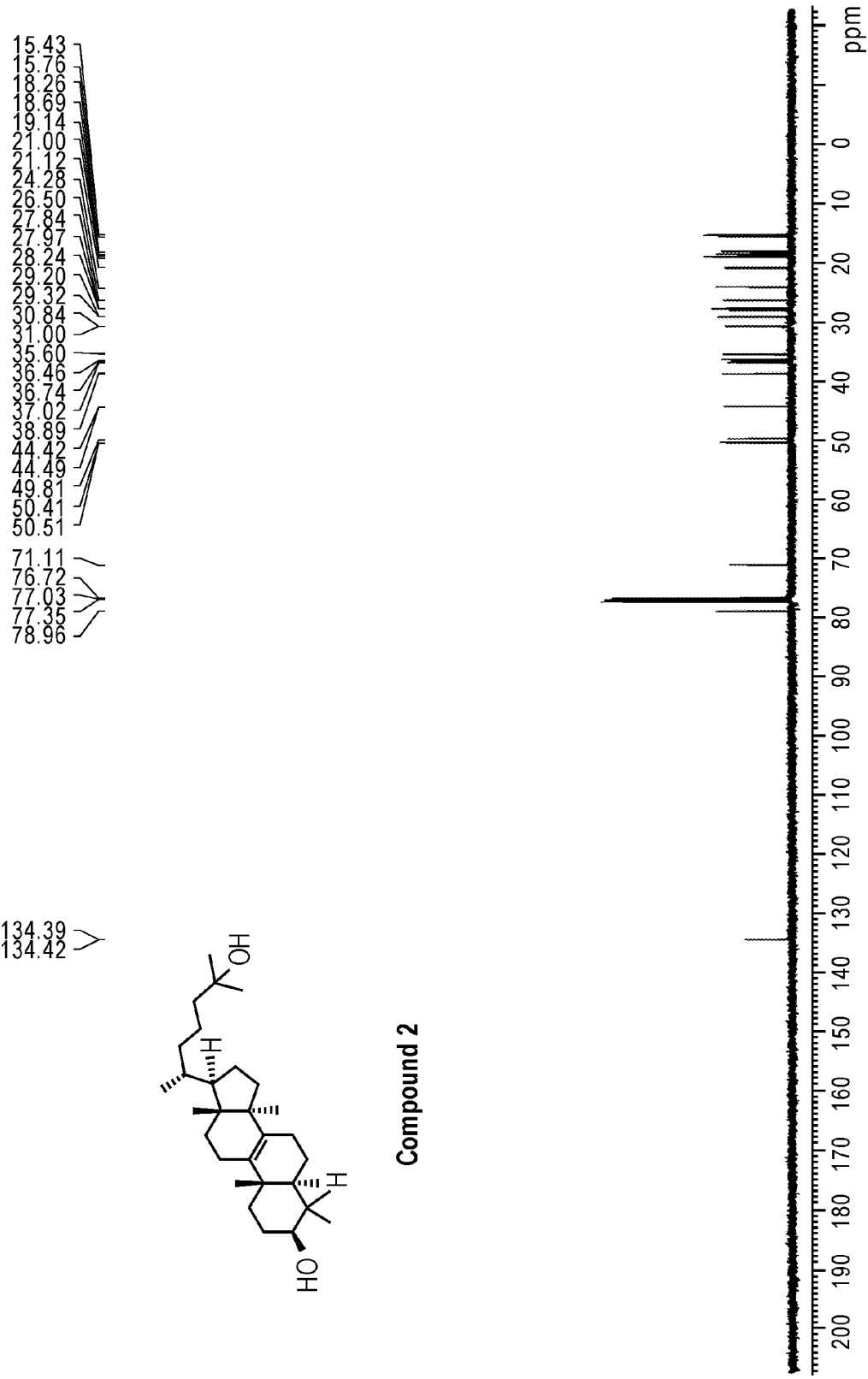

At 0° C., $LiAlH_4$ (32 g, 84.2 mmol) was dispersed in 300 mL dry THF. LS-6 (20 g, 41 mmol) was dissolved in 100 mL dry THF. At 0° C., the THF solution of LS-6 was added dropwise into the $LiAlH_4$ suspension. The reaction mixture was maintained at 0° C. for 3 h after addition was completed. A small amount of water was carefully added until no gas evolution was observed to make sure all the leftover $LiAlH_4$ was destroyed. Then the mixture was filtered through a short column of anhydrous $NaCO_3$ to remove the aluminum salts. The solution was concentrated to ca. 100 mL volume. Then 300 mL $CH_2Cl_2$ was added to dilute the solution. The solution was washed sequentially with 5% HCl (1×300 mL), saturated $NaHCO_3$ (2×300 mL), and brine (1×300 mL). The solution was dried by $Na_2SO_4$. Solvents were removed under reduced pressure to provide crude product. Toluene recrystallization provided Compound 2 (12.84 g, 70% yield). FIG. 4A shows the $^1H$ NMR of Compound 2 while FIG. 4B shows the $^{13}C$ NMR of Compound 2.

Figure 5A:
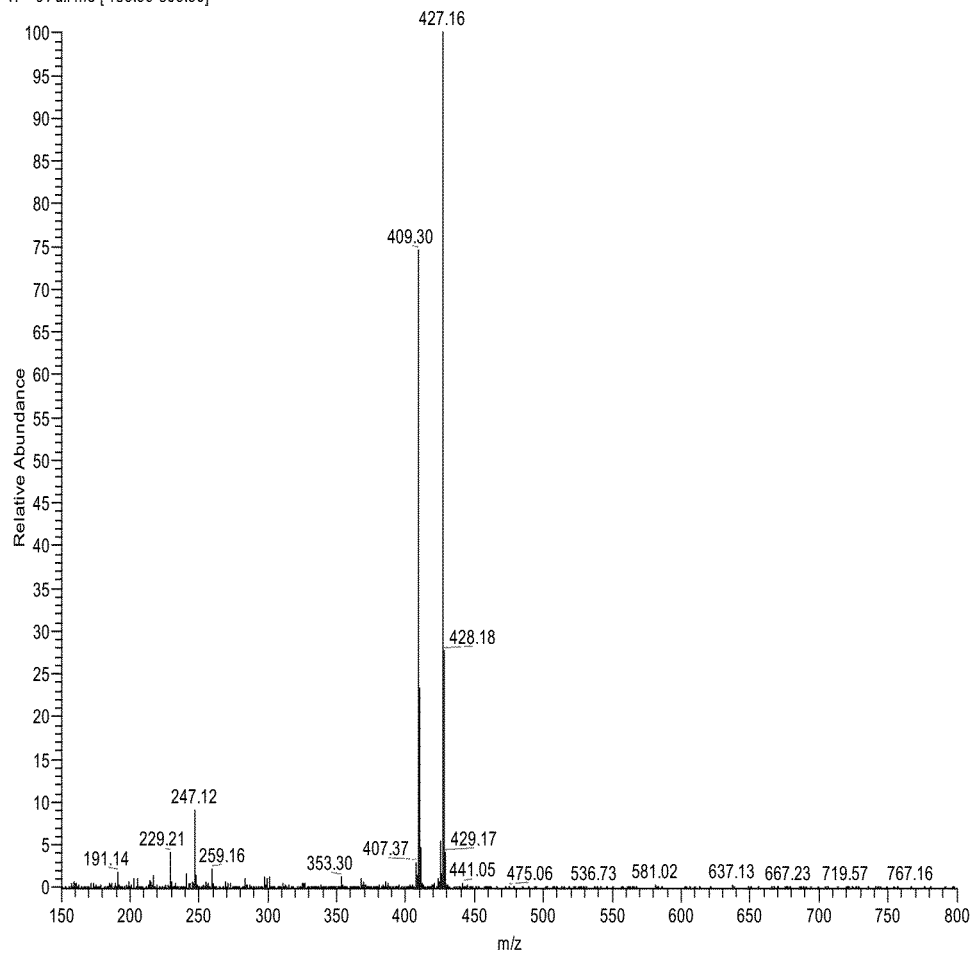
FIGS. 5A and 5B show MS data for Compound 2.
Figure 5B:
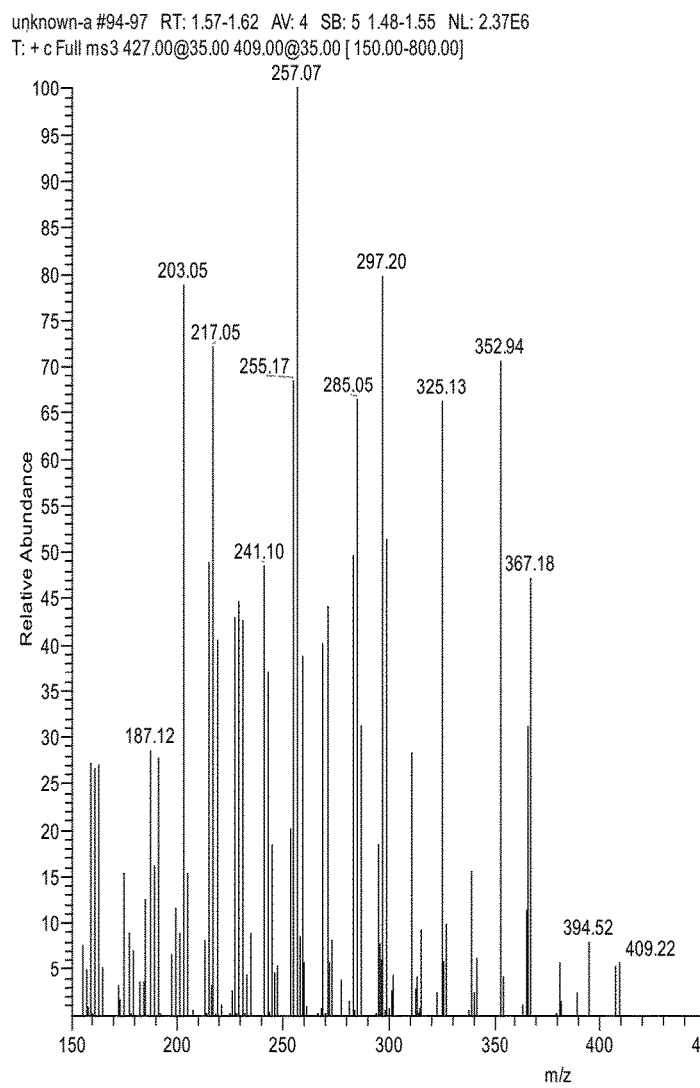

FIGS. 5A and 5B show the MS spectra obtained for the title compound.

Example 2
(3S,5R,10S,13R,14R,17R)-17-((2R)-5-bromo-6-hydroxy-6-methylheptan-2-yl)-4,4,10,13,14-pentamethyl-2,3,4,5,6,7,10,11,12,13,14,15,16,17-tetradecahydro-1H-cyclopenta[a]phenanthren-3-ol (Compound 1)
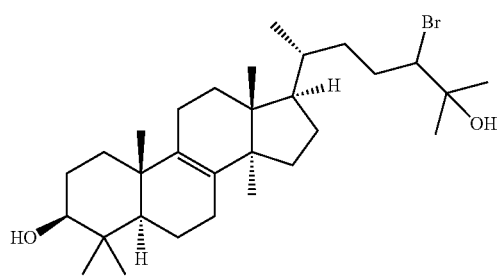 [SMILES: C[C@H](CCC(Br)C(C)(C)O)[C@H]1CC[C@@]2(C)C3=C(CC[C@]12C)[C@@]1(C)CC[C@H](O)C(C)(C)[C@@H]1CC3]
The synthetic sequence for Compound 1 is illustrated in Scheme 5 below.
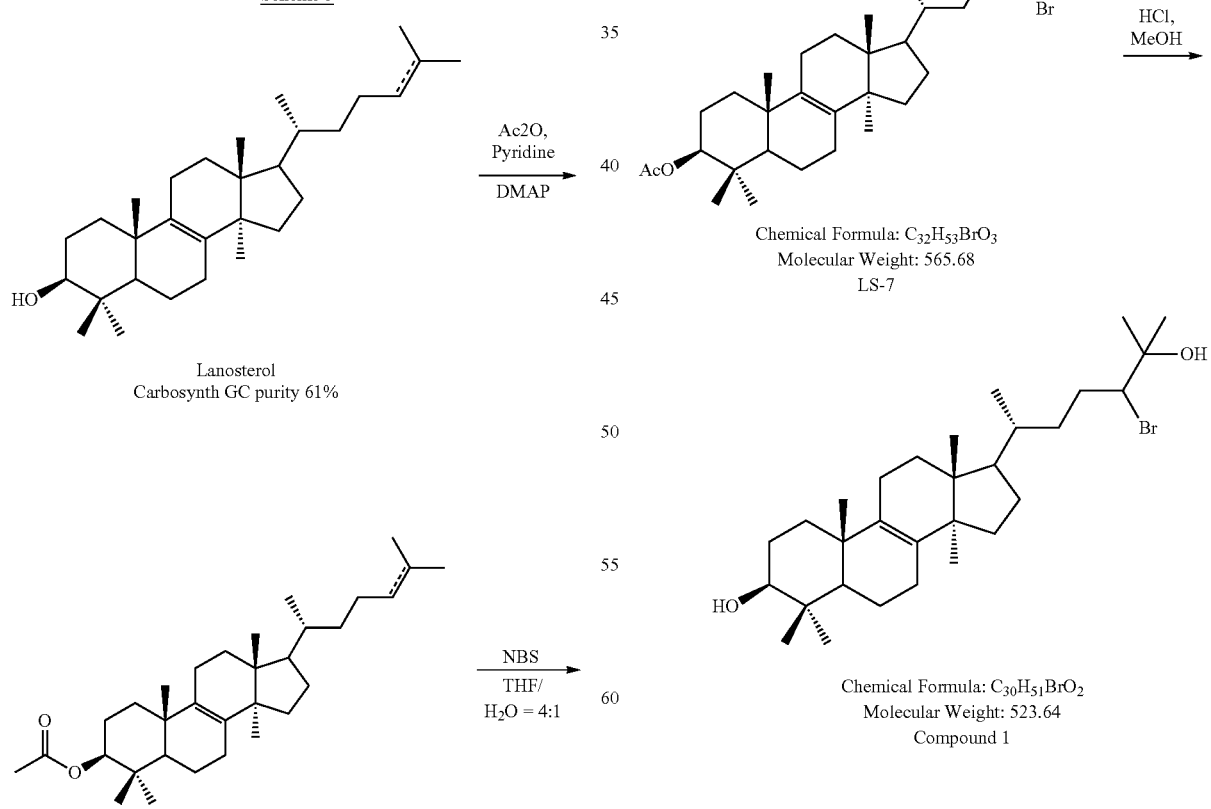
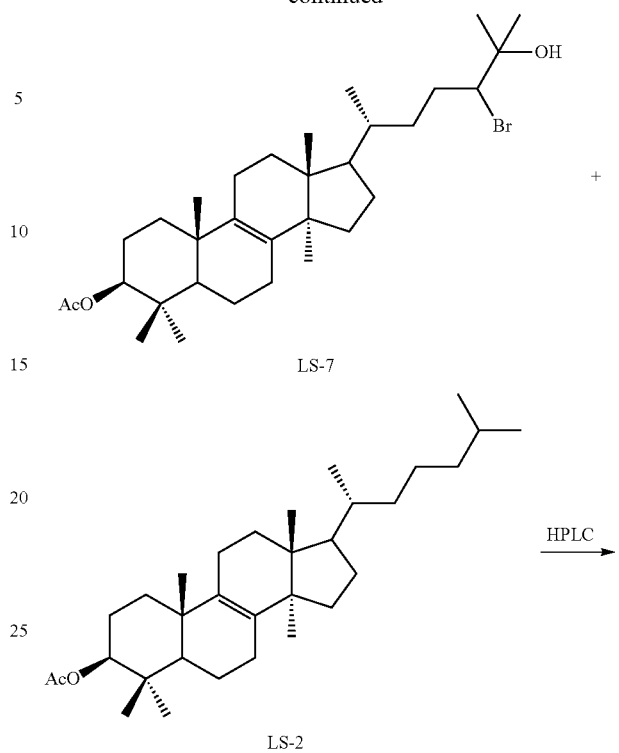
Step 1: Preparation of LS-1 and LS-2
LS-1 and LS-2 were prepared in the similar manner as described in Example 1.

Step 2: Preparation of LS-7 and LS-2

The LS-1 and LS-2 mixture (20 g, 42.6 mmol) was dissolved in THF/H$_2$O (4:1) 300 mL. At 0° C., NBS (9.10 g, 51.1 mmol) was added in portions. After completion of the addition, reaction mixture was aged at 0° C. for an additional 2.5 h. TLC was used to monitor the reaction. Then 300 mL EtOAc was added and solution was washed with saturated NaHCO$_3$ (1×300 mL) and brine (1×300 mL). The organic solution was dried with Na$_2$SO$_4$. Solvents were removed under vacuum to yield 18.8 g of LS-7 and LS-2.

Step 3: Purification of LS-7 and LS-2

Figure 6A:
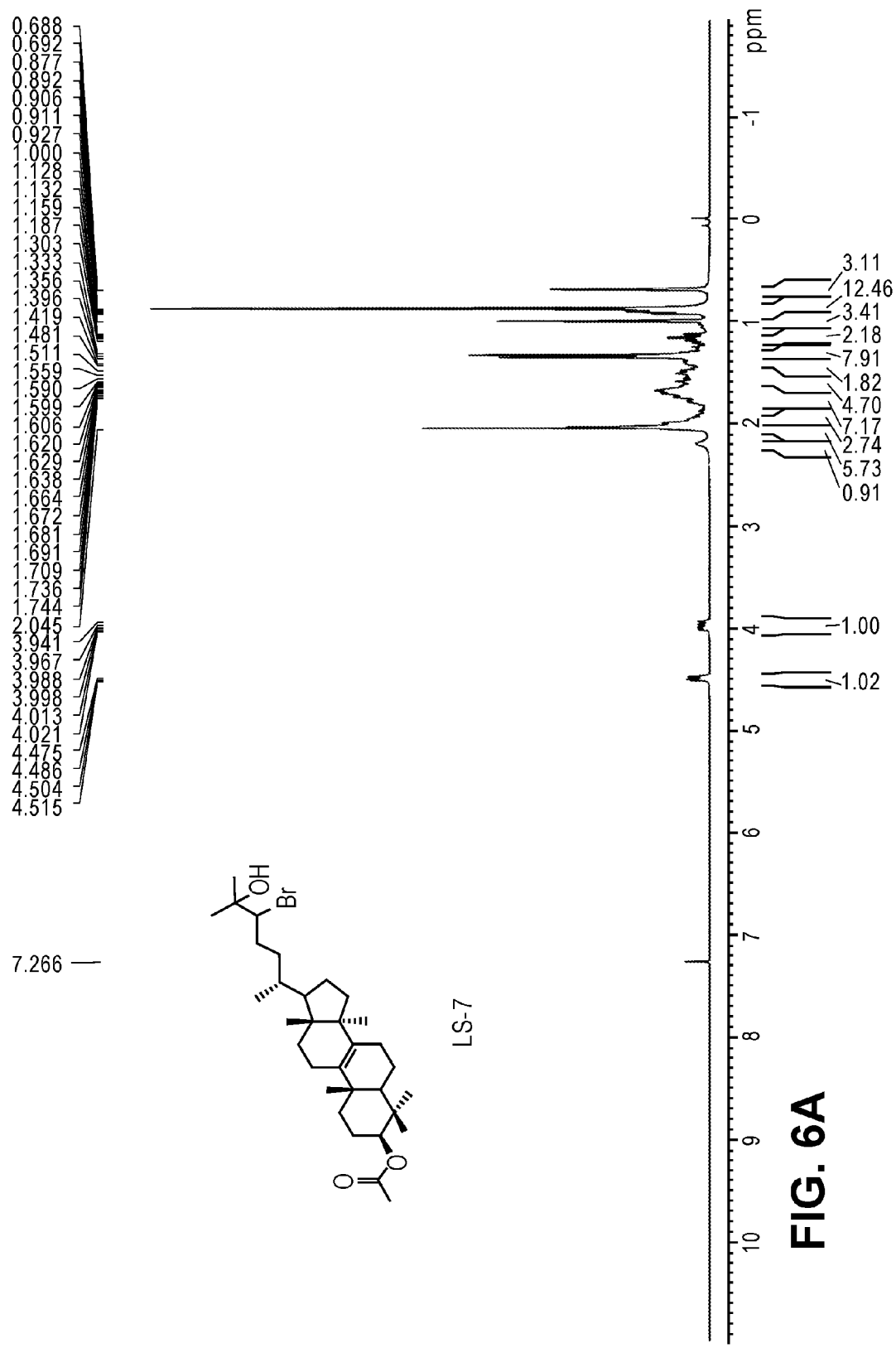
FIGS. 6A and 6B show the NMR data of LS-7.
Figure 6B:
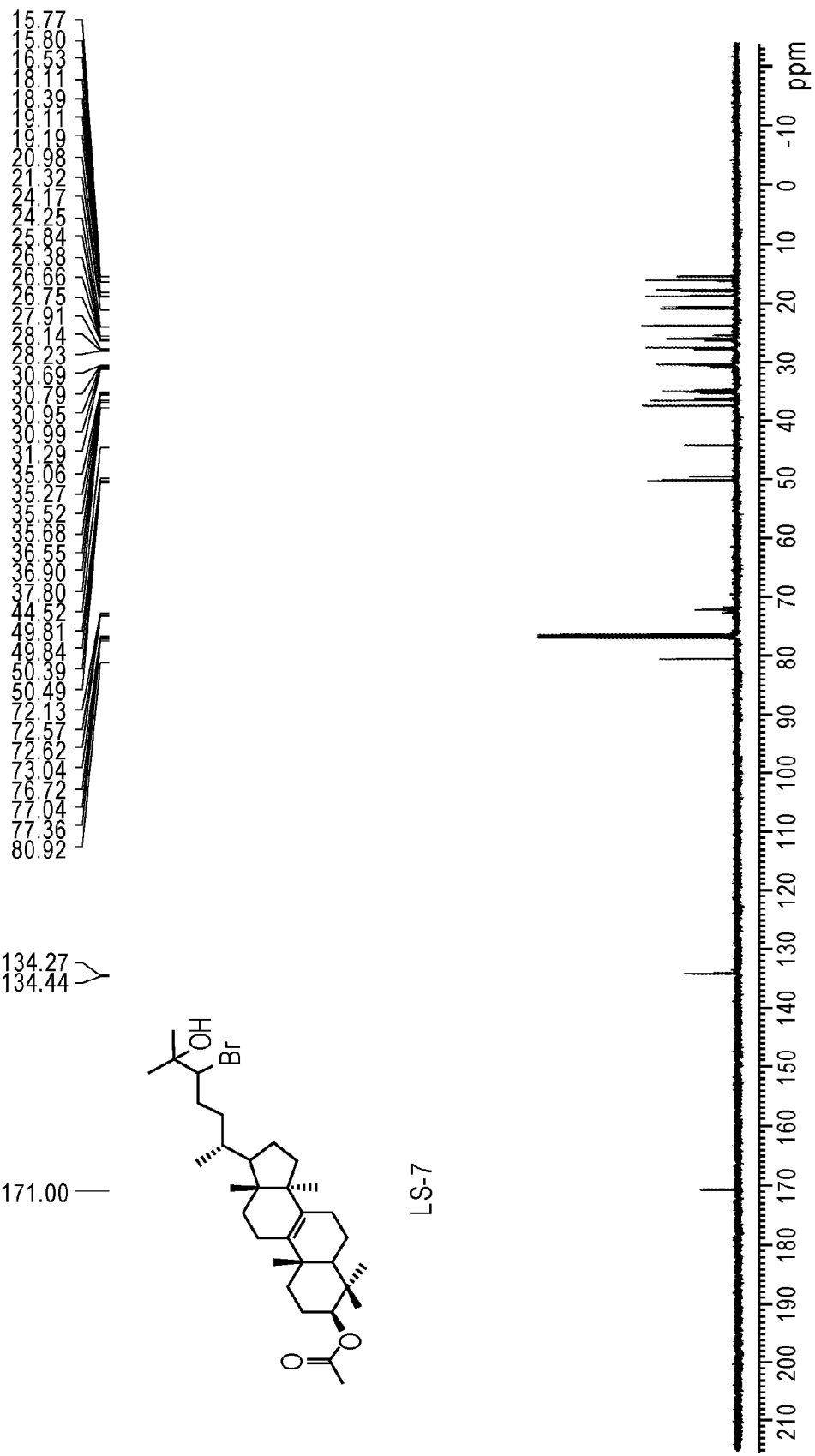

Prep-HPLC was used for the separation and purification of LS-7 and LS-2. FIG. 6A shows the $^1$H NMR of LS-7 while FIG. 6B shows the $^{13}$C NMR of LS-7.

Step 4: Preparation of Compound 1

LS-7 (16 g, 28.28 mmol) was dissolved into 150 mL MeOH. To this solution at 0° C., anhydrous HCl gas was slowly bubbled. Excess amount of HCl gas was bubbled through MeOH solution. The reaction solution was kept at 0° C. overnight. TLC was checked for completion of reaction. The MeOH was removed under reduced pressure and the residue was dissolved in 200 mL EtOAc. The organic solution was washed sequentially with saturated NaHCO$_3$ (2×200 mL) and brine (1×200 mL). The solution was dried with Na$_2$SO$_4$. Solvents were removed under reduced pressure to yield the crude product, which was then recrystallized in MeOH to provide Compound 1.

Figure 7A:
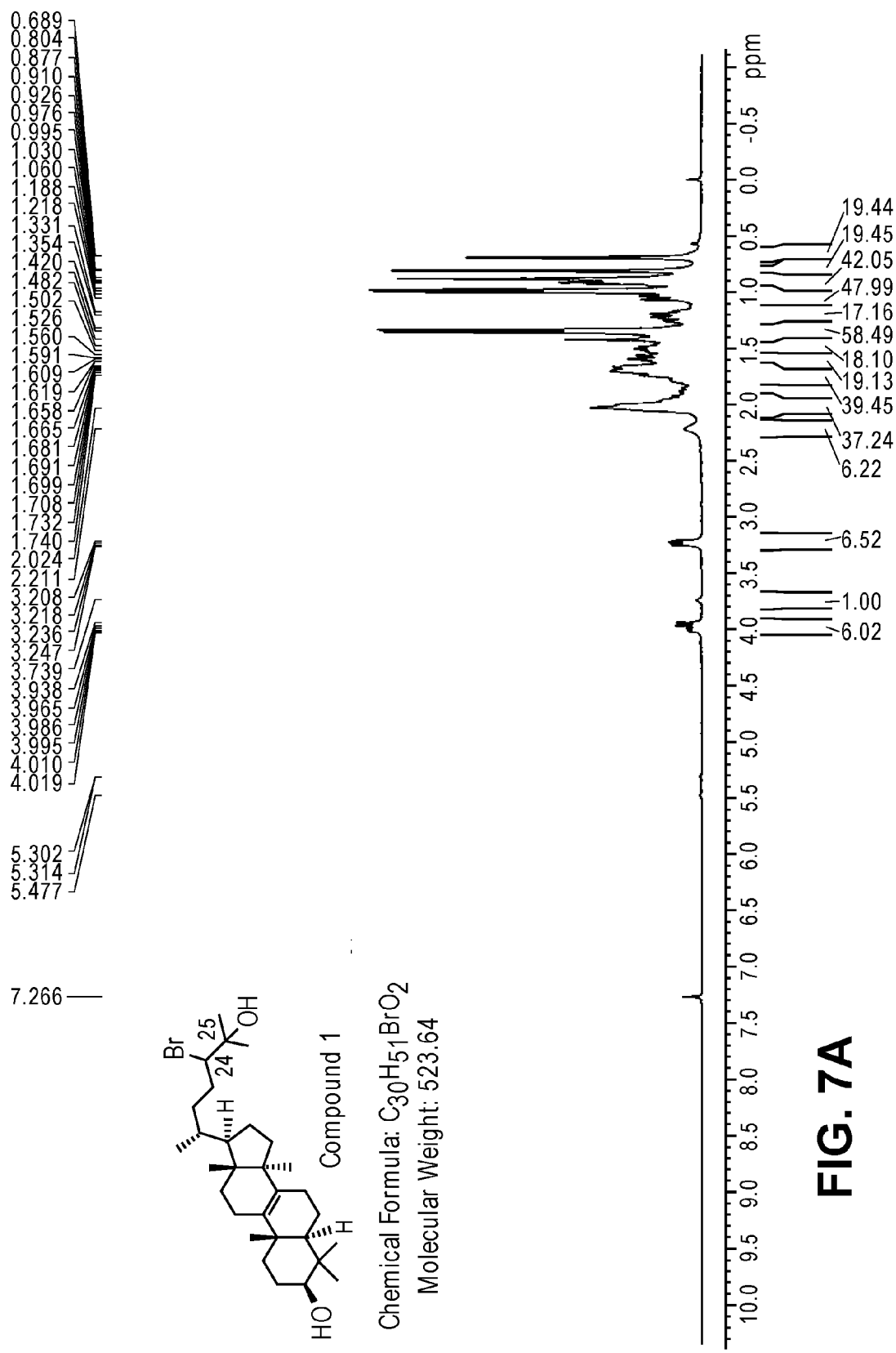
FIGS. 7A and 7B show the NMR data of Compound 1.
Figure 7B:
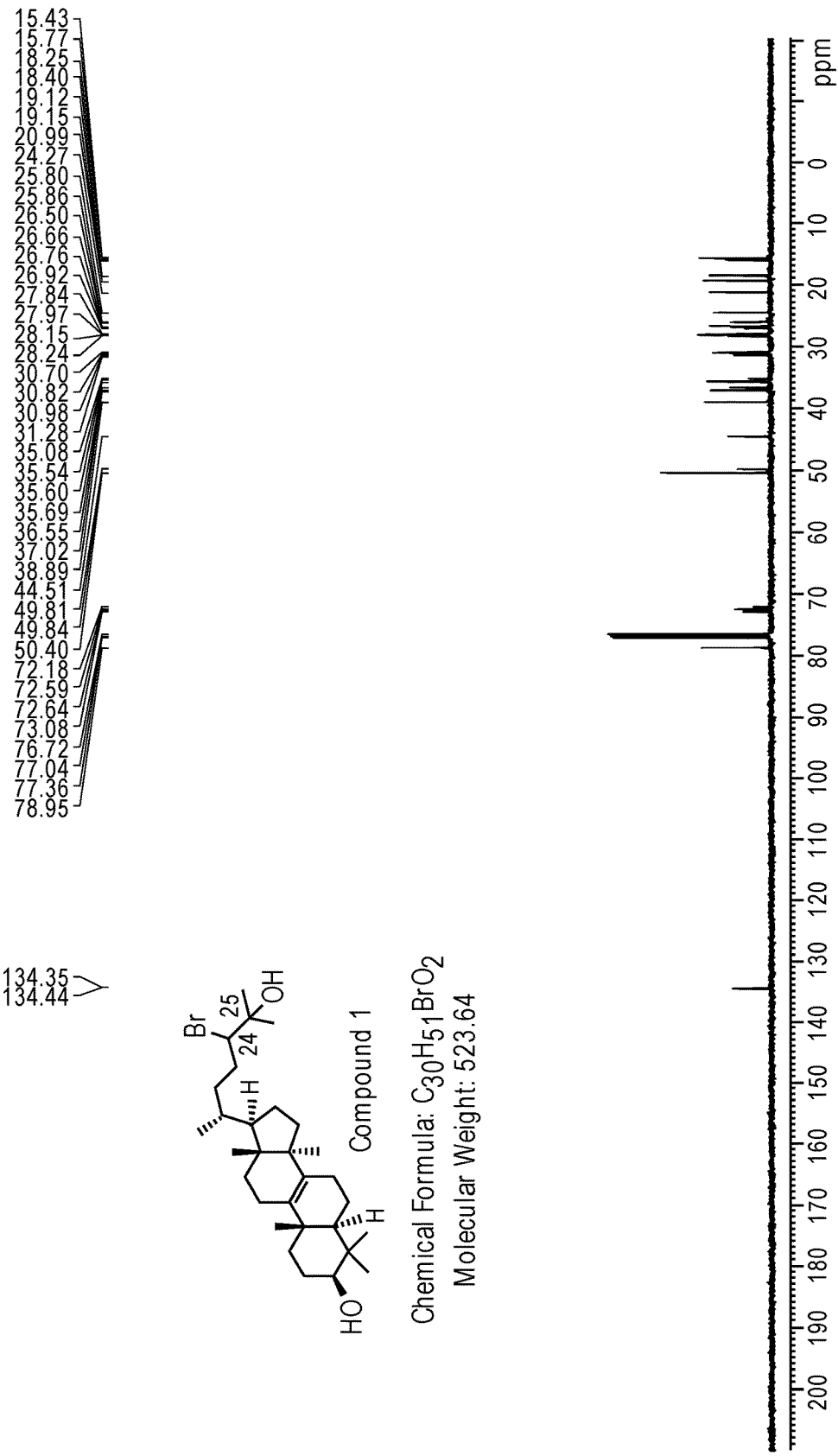
Figure 8:
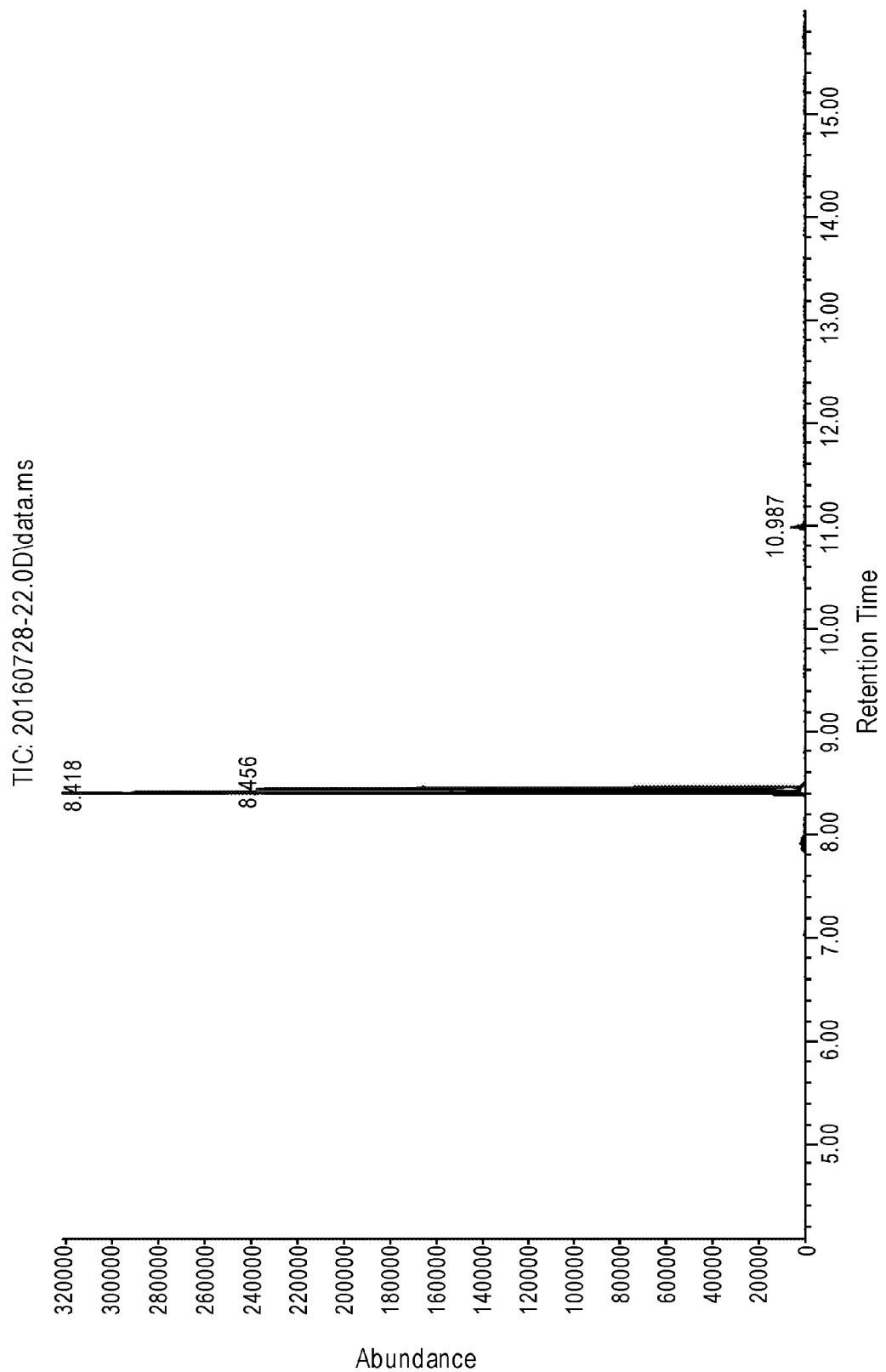
FIG. 8 shows the GC spectra of Compound 1.

FIG. 7A shows the $^1$H NMR of Compound 1 while FIG. 7B shows the $^{13}$C NMR of Compound 1. FIG. 8 shows the GC spectra of Compound 1.

Example B1

Cellular Aggregation Assay

Figure 9:
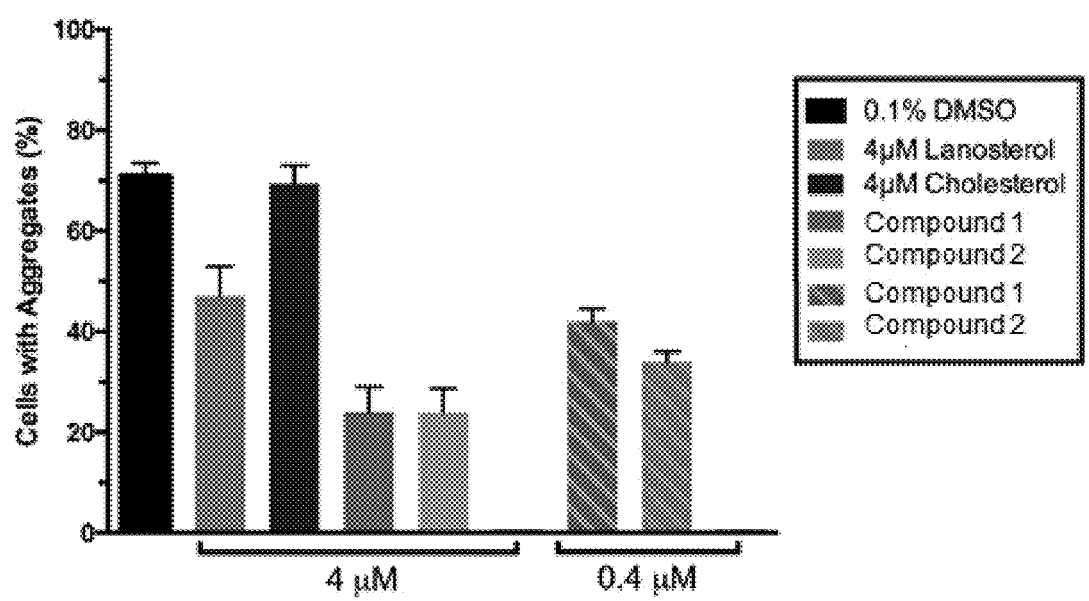
FIG. 9 shows cellular aggregation assay data for Compounds 1 and 2.
Figure 10:
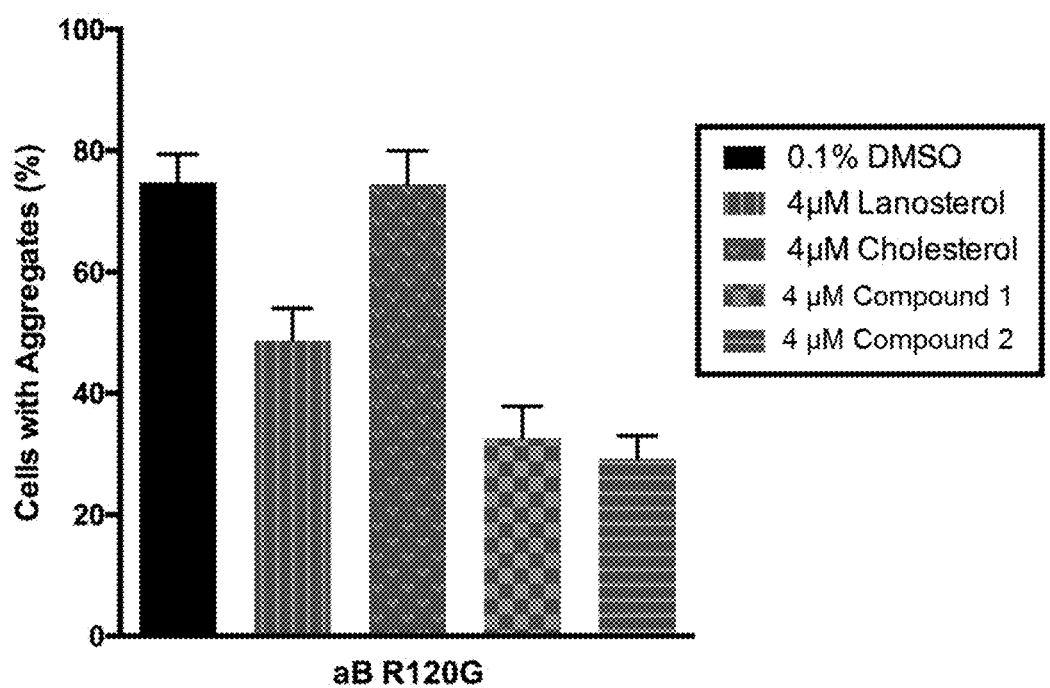
FIG. 10 shows cellular aggregation assay data for Compounds 1 and 2 on a crystallin mutant model (αB R120G).
Figure 12:
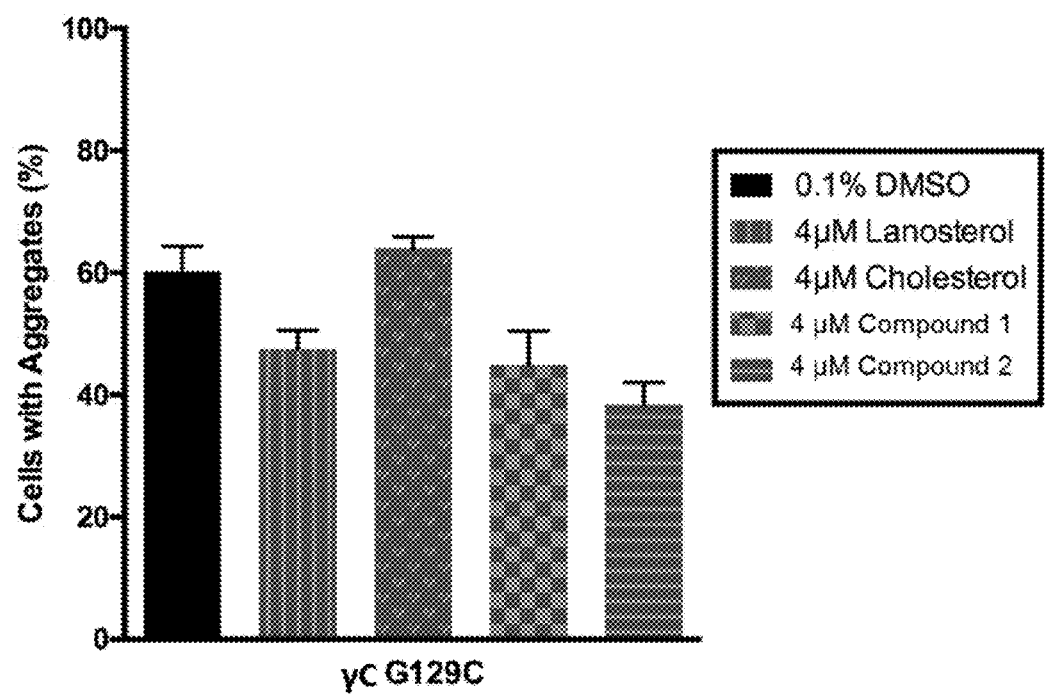
FIG. 12 shows cellular aggregation assay data for Compounds 1 and 2 on a crystallin mutant model (γC G129C).

FIGS. 9, 10, and 12 show the cellular aggregation assay for Compounds 1 and 2. FIG. 9 shows cellular aggregation assay data for Compounds 1 and 2.

Representative confocal images of HeLa cells transfected with a cataract-causing crystallin mutant-EGFP fusion construct (αB-crystallin R120G or γC-crystallin G129C) for 4 h and cultured for additional 24 h in a new culture medium. Then the cells were treated with 4 µM lanosterol, 4 µM cholesterol, compound 1, or compound 2 in 2% DMSO for 2 hours and cultured for another 12 h. Cells treated with 2% DMSO were used as a negative control. Formation of intracellular aggregates of crystallin proteins was visualized by fluorescence of GFP (green). The percentage of cells with crystallin aggregates was calculated from ten randomly selected viewing fields.

Figure 11:
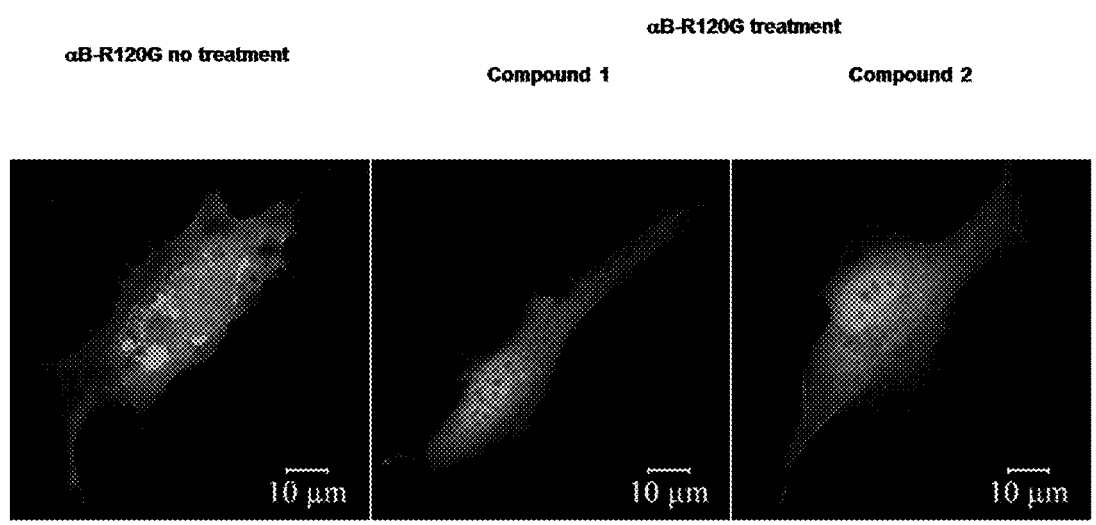
FIG. 11 shows the visualization of intracellular aggregates of crystallin proteins by GFP (green) fluorescence of HeLa cells after treatment with Compounds 1 and 2 on a crystallin mutant model (αB R120G).

FIG. 10 shows cellular aggregation assay data for Compounds 1 and 2 in a crystallin mutant model (αB R120G). FIG. 11 shows the visualization of intracellular aggregates of crystallin proteins by GFP (green) fluorescence of HeLa cells after treatment with Compounds 1 and 2 on a crystallin mutant model (αB R120G).

Figure 13:
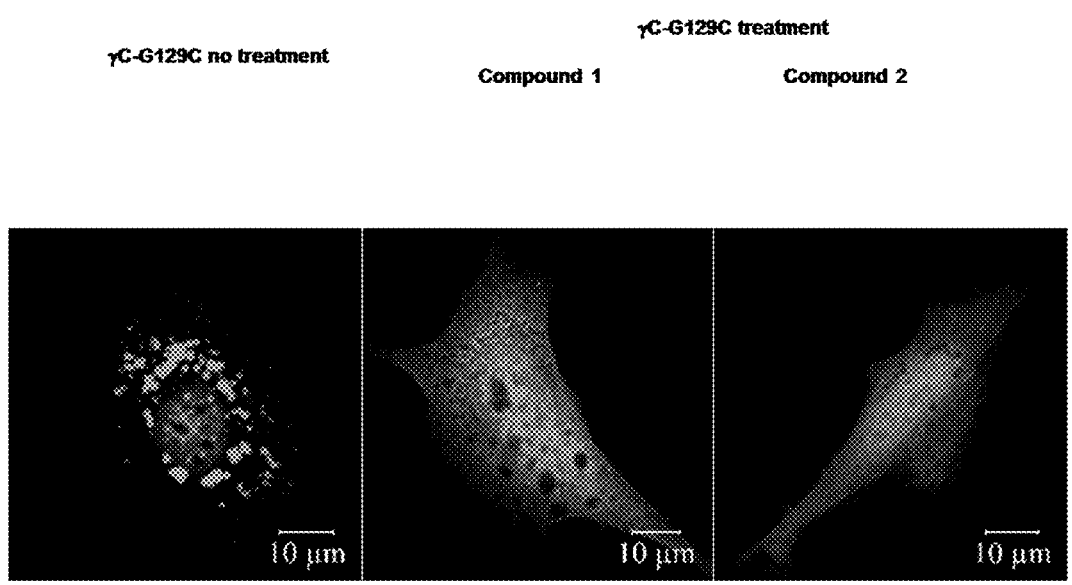
FIG. 13 shows the visualization of intracellular aggregates of crystallin proteins by GFP (green) fluorescence of HeLa cells after treatment with Compounds 1 and 2 on a crystallin mutant model (γC-crystallin G129C).

FIG. 12: shows data cellular aggregation assay for Compounds 1 and 2 in a crystallin mutant model (γC G129C). FIG. 13 shows the visualization of intracellular aggregates of crystallin proteins by GFP (green) fluorescence of HeLa cells after treatment with Compounds 1 and 2 on a crystallin mutant model (γC-crystallin G129C).

Example B2

Cataract Studies

Figure 14A:
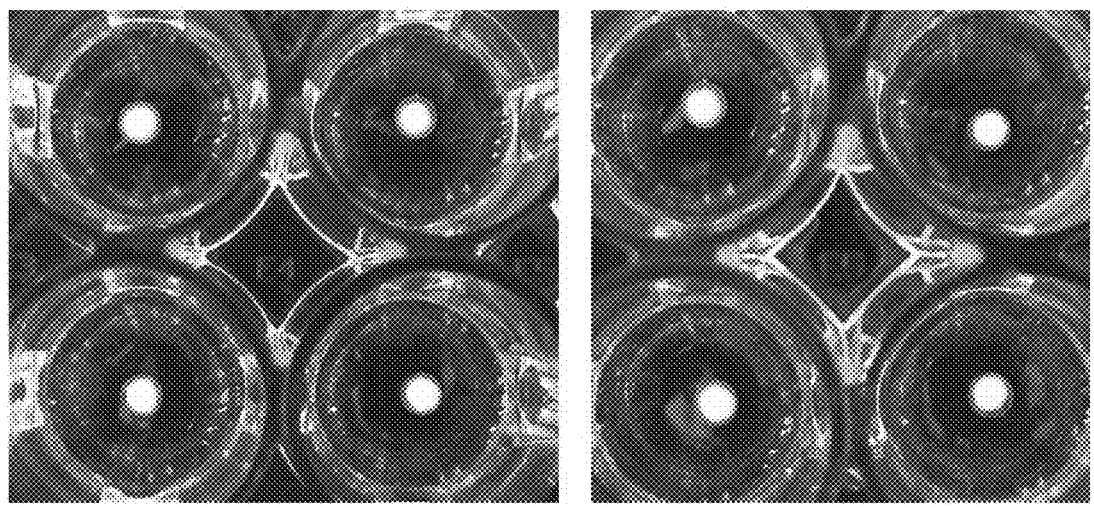
FIGS. 14A and 14B show cataract lenses that have been treated with Compound 1.
Figure 14B:
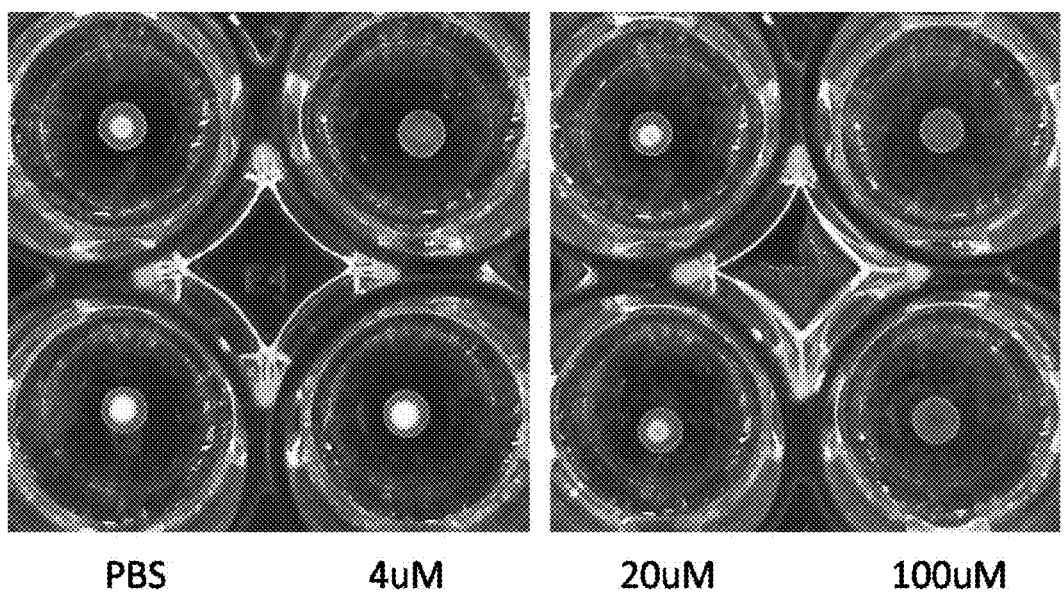

FIGS. 14A and 14B show cataract lenses that have been treated with Compound 1. FIG. 14A show mouse lenses (white) that were dissected from the eye and placed into phosphate buffered saline solution (PBS) overnight at 4° C. Cataract was visible in all lenses. The cataract lenses were incubated with Compound 1 at the indicated concentration for 4 hours at room temperature and then scored for clarity. FIG. 14B shows the mouse lenses after treatment with Compound 1 at the indicated concentrations. The PBS solution served as negative control and there were no lens opacity change. Increased lens clarity and reduced cataract was observed in lenses treated with Compound 1.

Figure 15A:
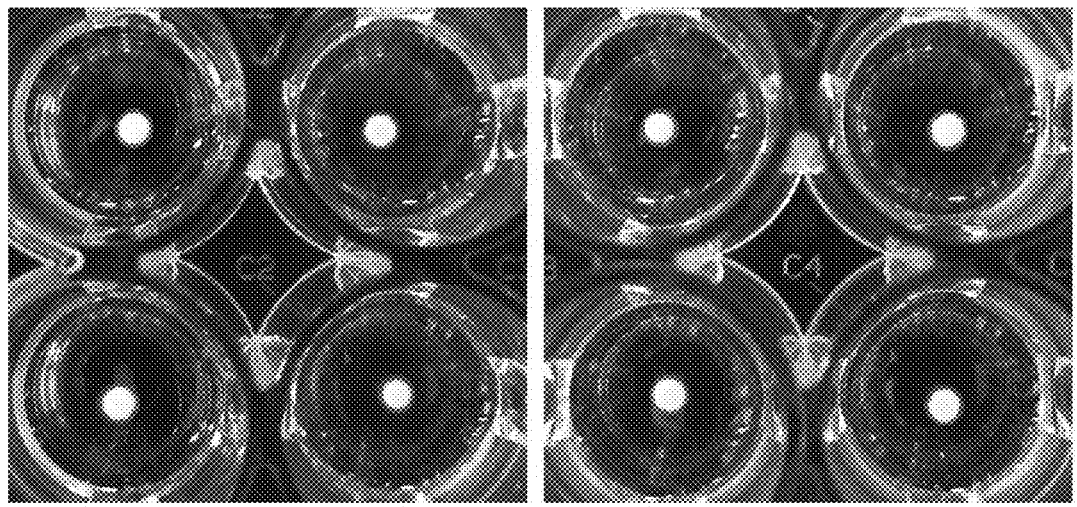
FIGS. 15A and 15B show cataract lenses that have been treated with Compound 2.
Figure 15B:
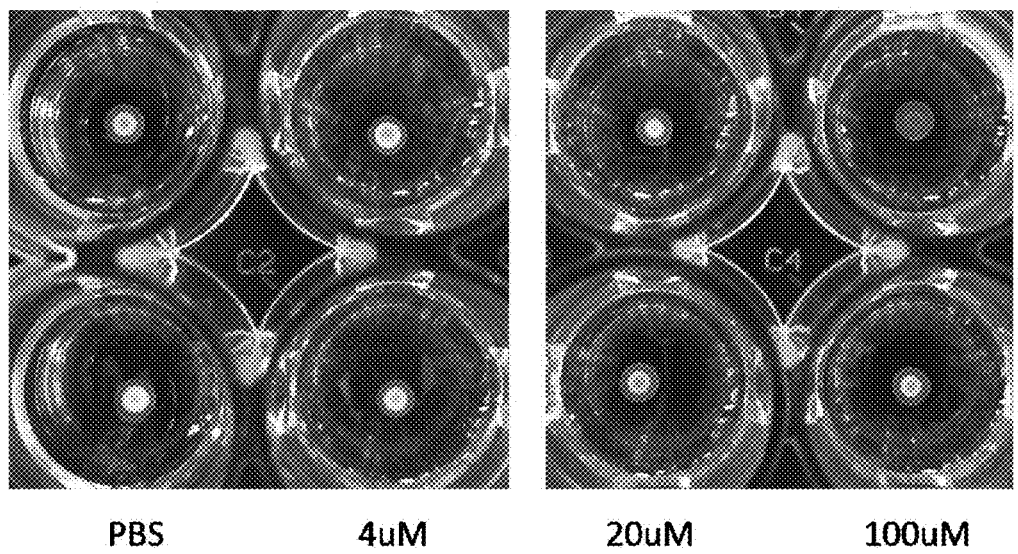

FIGS. 15A and 15B show cataract lenses that have been treated with Compound 2. FIG. 15A show mouse lenses (white) that were dissected from the eye and placed into phosphate buffered saline solution (PBS) overnight at 4° C. Cataract was visible in all lenses. The cataract lenses were incubated with Compound 2 at the indicated concentration for 4 hours at room temperature and then scored for clarity. FIG. 15B shows the mouse lenses after treatment with Compound 2 at the indicated concentrations. The PBS solution served as negative control and there were no lens opacity change. Increased lens clarity and reduced cataract was observed in lenses treated with Compound 2.

Figure 16A:
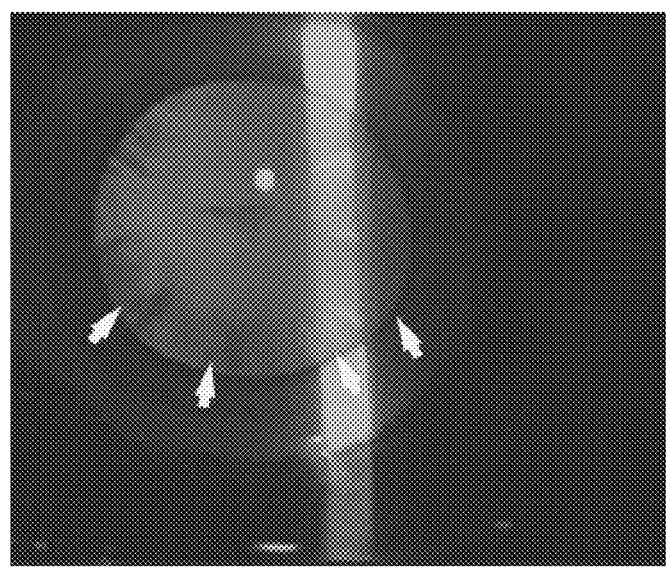
FIGS. 16A and 16B show the result of mouse eyes treated with an eye drop solution containing Compound 1 at 100 μm concentration three times a day for 50 μl each time for 6 weeks.
Figure 16B:

FIGS. 16A and 16B show the result of mouse eyes treated with an eye drop solution containing Compound 1 at 100 µM concentration three times a day for 50 µl each time for 6 weeks. FIG. 16A shows the negative control and FIG. 16B shows the treated eye, which shows increased clarity and reduced cataract.

Example B3

Aggresome Formation

The effect of any one of the compounds disclosed herein on aggresome formation of various crystallins is studied by transfecting the cells with plasmids containing various crystallin genes. The cells are incubated for an appropriate amount of time, such as 24 h, to allow for efficient protein expression and aggresome formation. The cells are then treated with an appropriate amount of any one of the compounds disclosed herein at an appropriate concentration (such as 0-40 mM in 1% for human lens progenitor cells or 2% DMSO for HeLa cells). Cells treated with 1% or 2% DMSO are used as the control. After treatment for an appropriate amount of time, such as 2 h, the media is replaced with fresh media. After a suitable amount of time, such as 12 h, the cells are prepared for microscopic analysis.

Microscopy samples are prepared by washing the slips with phosphate buffered saline (PBS) three times. The cells are then fixed with 4% paraformaldehyde for about 40 min followed by another three washes with PBS. The cells are then permeabilized with 0.1% Triton X-100 (Sigma) in PBS for about 10 min and blocked with 5% normal goat serum in PBS for 1 h at 37° C. Immunostaining is carried out by adding mouse anti-Flag antibody (1:500) or mouse anti-p62 antibody (1:200, ab56416; Abcam) in PBS buffer containing 5% normal goat serum and incubated for about 1 h at about 37° C. The slips are washed three times with PBS, and further incubated with Alexa 649-conjugated goat anti-mouse IgG (1:250) for 1 h at ambient temperature. The nuclei are counterstained with Hoeschst 33342 (Invitrogen). The mounted cells are analyzed using a Carl Zeiss LSM 710 confocal microscope.

Example B4

Live Cell Imaging

Human lens progenitor cells are transfected with plasmids containing αA-crystallin (Y118D) mutant. After a suitable amount of time for transfection, such as 24 h, the cells with stable expression of αA-crystallin (Y118D) are screened by incubation in a suitable culture medium, such as a medium containing 0.8 mg/ml G418, for a suitable period, such as 7 days. The obtained cells are then seeded onto glass bottom cell culture dishes (In Vitro Scientific) and treated with vehicle, such as 1% DMSO, or any one of the compounds disclosed herein dissolved in the vehicle, such as 40 nM of test compound in 1% DMSO, for a suitable amount of time, such as 4 h. Fresh culture medium is then added and the cells are analyzed by serial live-cell imaging.

Live-cell images are viewed with an Olympus IX81 microscope and captured with CellSens Dimension software (Olympus). Quantitative analysis of the size of aggregates is performed by measuring the fluorescence intensity of the p62-positive aggregates using single particle tracking in live-cell imaging. The live cell imaging is conducted using three biological replicates with 1-8 repetitions each.

Example B5

Protein Aggregation and Aggregate Dissociation

The aggregates of wild-type and mutated αA- and αB-crystallin proteins are obtained by heating the protein solutions containing a suitable amount of guanidine chloride (such as 1M; ultrapure, Sigma-Aldrich) at a suitable concentration for an appropriate time and temperature, such as 5 mg/ml at 60° C. for 2 h. The aggregate of the wild-type and mutated b- and c-crystallins are prepared by heating the protein solutions containing a suitable amount of guanidine chloride, such as 1 M, at an appropriate time and temperature, such as at 37° C. for 48 h. The formation of aggregates is confirmed by ThT fluorescence, turbidity (absorbance at 400 nm) and transmission electron microscopy (TEM). The preformed aggregates are then resuspended in 20 mM PBS with a suitable final concentration, such as 0.2 mg/ml (approximately 10 mM). The re-suspended aggregates are then treated with an appropriate amount of any one of the compounds disclosed herein in a suitable vehicle, such as liposomes formed by 500 mM DPPC (Sigma-Aldrich) at 37° C. In some instances, a suitable negative control is treatment of the vehicle without the test compound. After a suitable amount of time, such as 24 h after treatment, the protein solutions are used for ThT fluorescence, turbidity and negatively stained TEM. The TEM samples are prepared by depositing the protein solution onto a freshly glow-discharged carbon-coated copper grid. Negative-staining samples are obtained by staining the grid with 1.25% uranyl acetate for about 30 s. The negatively stained TEM pictures are obtained on a Hitachi H-7659B transmission electron microscope with an appropriate voltage, such as 120 kV, and a suitable magnification, such as 48,000.

Example B6

Treatment of Cataractous Lenses in Rabbits

Rabbits are euthanized by $CO_2$ inhalation and lenses are dissected and treated with a suitable vehicle or any one of the compounds disclosed herein dissolved in a suitable vehicle in a suitable concentration (such as 25 mM). Lens tissues are incubated in these solutions for about 6 days in the dark at room temperature. Cataracts are examined under a microscope and photographed. The degree of cataract is assessed by a blinded examiner using the opacification grading system as described below. Improvements in lens clarity and transparency are quantified by visual inspection and grading. Lens clarity is scored by transmission of light, clarity of a grid image underneath the lens and improvement in overall clarity of a lens or improvement in clarity of localized areas of cortical cataract. Wilcoxon test is used to evaluate the treatment effect.

Cataract grading system: Grade 0: absence of opacification (gridlines clearly visible); N Grade 1: a slight degree of opacification (minimal clouding of gridlines, with gridlines still visible); N Grade 2: presence of diffuse opacification involving almost the entire lens (moderate clouding of gridlines, with main gridlines visible); and N Grade 3: presence of extensive, thick opacification involving the entire lens (total clouding of gridlines, with gridlines not seen at all).

Example B7

Treatment of Cataractous Lenses in Dogs

Dogs are pre-medicated with intramuscular injections of acepromaxine and butorphanol. After about 20 min, induction of anaesthesia is performed by application of intravenous propofol. Dogs are then immediately intubated and maintained on oxygen and 2% isoflurane at about 21 min$^{-1}$. Any one of the compounds disclosed herein is dissolved in an appropriate vehicle, and is then injected into the vitreous cavity in the test eye using a 28-gauge needle, and is then administered at appropriate intervals for the duration of the experiments (such as every 3 days over a 6 week period). Eyes treated with any one of the compounds disclosed herein or with an appropriate control are randomized. A negative control is the administration of the suitable vehicle in the absence of the test compound. In some embodiments, a suitable vehicle is prepared from adding double distilled water to an appropriate amount of $(EDTA)_2Na$ (such as 1.1 g) combined with an appropriate amount alkyldimethylbenzylammonium chloride (such as 0.055 g) to provide the desired total volume and pH (such as 1.1 L at pH of 5.66).

The degree of cataract severity is examined by slit lamp and photographed at the beginning and at the end of the treatment period. Prior to the examination, pupils are dilated with 1% tropicamide and 10% phenylephrine. The degree of cataract is assessed by a blinded examiner using the canine cataract grading system as described below. Improvements in lens clarity and transparency are quantified. Wilcoxon test is used to evaluate the treatment effect.

Canine Cataract grading system: Grade 0: absence of opacification (no cataract); N Grade 1: a slight degree of opacification (incipient stage); N Grade 2: presence of diffuse opacification involving almost the entire lens (immature stage); and N Grade 3: presence of extensive, thick opacification involving the entire lens (mature stage).

Embodiments

Embodiment 1: A compound of Formula (Ic):

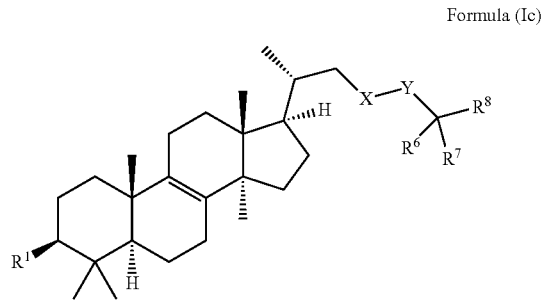

Formula (Ic)

or a pharmaceutically acceptable salt thereof,
wherein
X is —C(R$^4$)$_2$—;
each R$^4$ is independently hydrogen, —OR$^e$, optionally substituted C$_1$-C$_6$alkyl, or halogen;

each $R^e$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; Y is —C($R^5$)$_2$-;

each $R^5$ is independently hydrogen, —O$R^g$, optionally substituted $C_1$-$C_6$alkyl, or halogen; $R^g$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; each $R^6$, $R^7$, and $R^8$ is independently hydrogen, optionally substituted $C_1$-$C_6$alkyl, halogen, —O$R^h$, —S$R^h$, or N($R^i$)$_2$;

each $R^h$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^i$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^i$ are taken together with the N atom to which they are attached to form an optionally substituted heterocycloalkyl ring;

$R^1$ is —O$R^{10}$, —S$R^{10}$, —N($R^{10}$)$_2$, or halogen; and each $R^{10}$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycloalkyl ring.

Embodiment 2: The compound of embodiment 1, or the pharmaceutically acceptable salt thereof, wherein X is —CH$_2$— or —CH(O$R^e$)—.

Embodiment 3: The compound of embodiments 1 or 2, or the pharmaceutically acceptable salt thereof, wherein $R^e$ is hydrogen.

Embodiment 4: The compound of any one of embodiments 1-3, or the pharmaceutically acceptable salt thereof, wherein Y is —CH$_2$—, —CH(O$R^g$)—, or —CH($R^5$)—; and wherein $R^5$ is optionally substituted $C_1$-$C_6$alkyl or halogen.

Embodiment 5: The compound of embodiment 4, or the pharmaceutically acceptable salt thereof, wherein $R^g$ is hydrogen.

Embodiment 6: The compound of embodiment 4, or the pharmaceutically acceptable salt thereof, wherein $R^5$ is —Br or —F.

Embodiment 7: The compound of embodiment 4, or the pharmaceutically acceptable salt thereof, wherein $R^5$ is methyl or ethyl.

Embodiment 8: The compound of any one of embodiments 1-7, or the pharmaceutically acceptable salt thereof, wherein $R^6$ and $R^7$ are each independently $C_1$-$C_3$ alkyl.

Embodiment 9: The compound of embodiment 8, or the pharmaceutically acceptable salt thereof, wherein $R^6$ and $R^7$ are each independently methyl.

Embodiment 10: The compound of any one of embodiments 1-9, or the pharmaceutically acceptable salt thereof, wherein $R^8$ is hydrogen, —O$R^h$, or N($R^i$)$_2$.

Embodiment 11: The compound of embodiment 1, or the pharmaceutically acceptable salt thereof, having a Formula (Id):

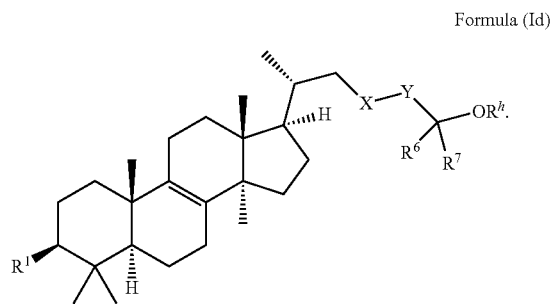

Formula (Id)

Embodiment 12: The compound of embodiment 11, or the pharmaceutically acceptable salt thereof, wherein $R^h$ is hydrogen.

Embodiment 13: The compound of embodiment 1, or the pharmaceutically acceptable salt thereof, wherein the compound is selected from:

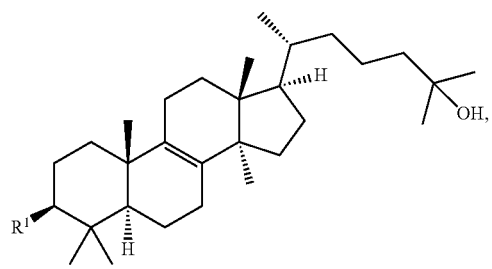

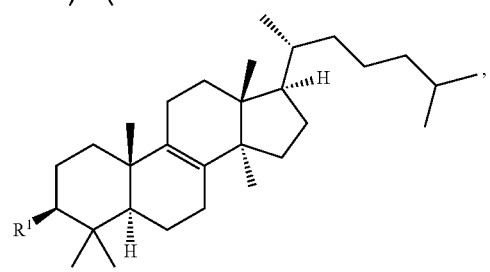

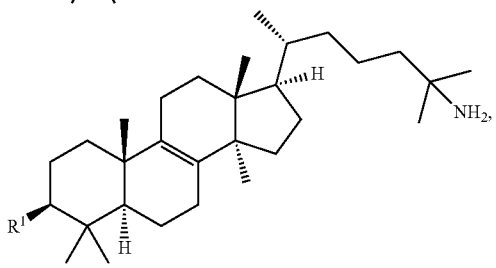

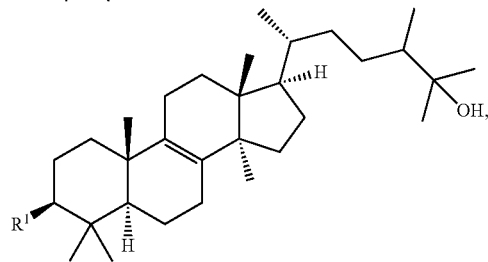

-continued

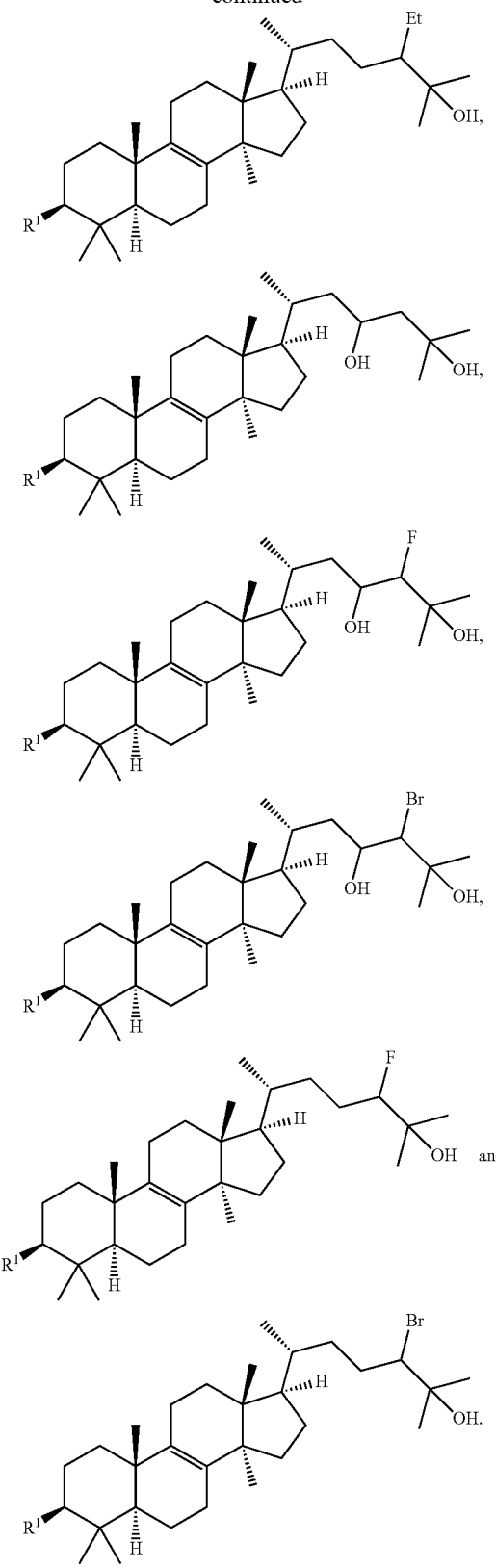

Embodiment 14: The compound of any one of embodiments 1-13, or the pharmaceutically acceptable salt thereof, wherein $R^1$ is —$OR^{10}$.

Embodiment 15: The compound of embodiment 14, or the pharmaceutically acceptable salt thereof, wherein $R^1$ is —OH, —OMe, —OEt, or —O-n-Pr.

Embodiment 16: The compound of embodiment 15, or the pharmaceutically acceptable salt thereof, wherein $R^1$ is —OH.

Embodiment 17: The compound of any one of embodiments 1-13, or the pharmaceutically acceptable salt thereof, wherein $R^1$ is —$SR^{10}$, or —$N(R^{10})_2$.

Embodiment 18: The compound of embodiment 17, or the pharmaceutically acceptable salt thereof, wherein $R^1$ is —$NH_2$, —NH(Me), —$N(Me)_2$, —NH(Et), or —SH.

Embodiment 19: The compound of any one of embodiments 1-13, or the pharmaceutically acceptable salt thereof, wherein $R^1$ is halogen.

Embodiment 20: The compound of embodiment 19, or the pharmaceutically acceptable salt thereof, wherein $R^1$ is —Br.

Embodiment 21: The compound of embodiment 1, or the pharmaceutically acceptable salt thereof, wherein the compound is selected from:

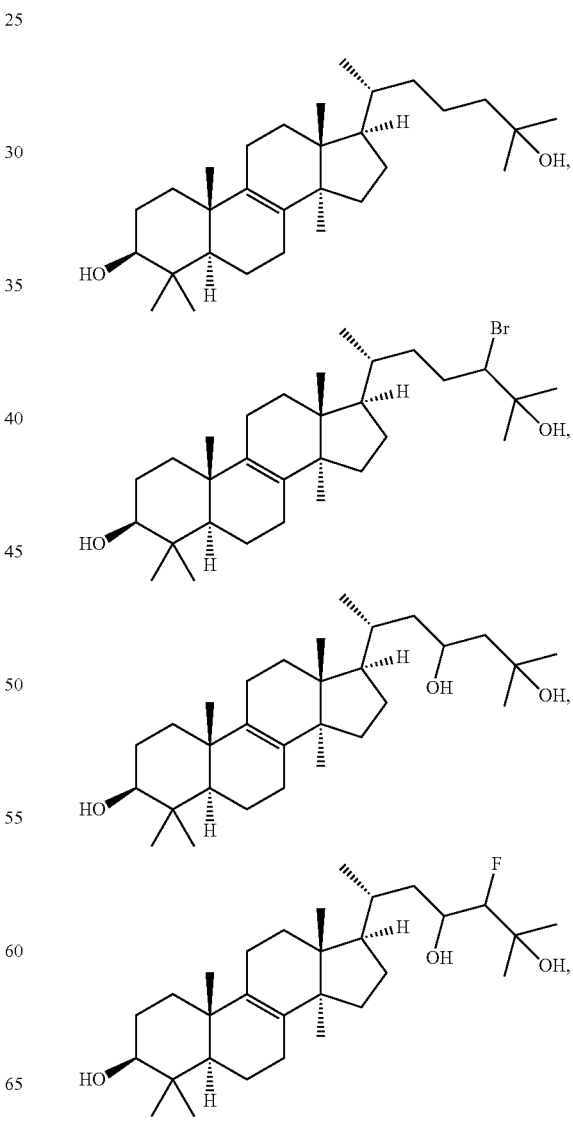

-continued

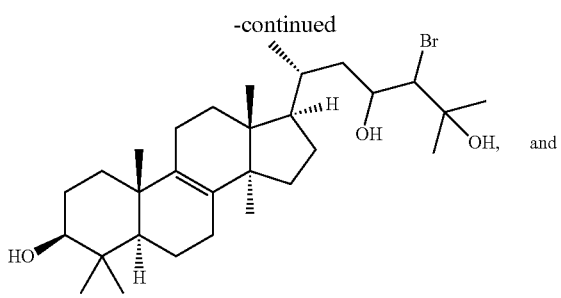

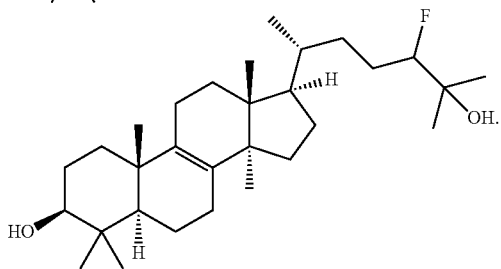

Embodiment 22: The compound of embodiment 21, or the pharmaceutically acceptable salt thereof, wherein the compound is selected from:

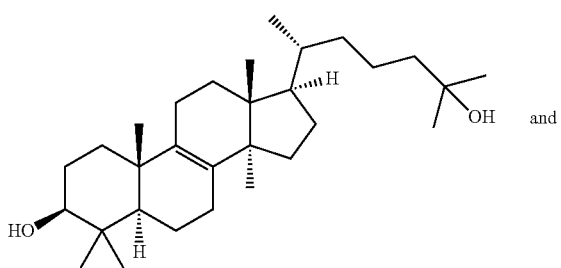

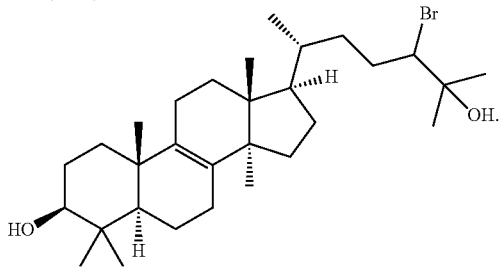

Embodiment 23: A pharmaceutical composition comprising the compound of any one of embodiments 1-22, or a pharmaceutically acceptable salt thereof, and a pharmaceutically acceptable excipient.

Embodiment 24: A method of treating a disease or disorder in a subject in need thereof, comprising administering a therapeutically effective amount of the compound of any one of embodiments 1-22, or a pharmaceutically acceptable salt thereof.

Embodiment 25: The method of embodiment 24, wherein the disease or disorder is an eye disease or disorder.

Embodiment 26: The method of embodiment 25, wherein the eye disease or disorder is selected from the group consisting of cataract, congenital cataracts, cortical opacities, posterior subcapsular cataract, presbyopia nuclear sclerosis, retinal degenerative disorder, Refsum disease, Smith-Lemli-Opitz syndrome, Schnyder crystalline corneal dystrophy, drusen, age-related macular degeneration, and diabetic retinopathy.

Embodiment 27: The method of any one of embodiments 24-26, wherein the compound, or the pharmaceutically acceptable salt thereof, inhibits or prevents protein aggregation.

Embodiment 28: The method of embodiment 27, wherein the protein is an amyloid-forming protein.

Embodiment 29: The method of embodiment 28, wherein the amyloid-forming protein is selected from Hsp27, αA-crystallin, αB-crystallin, ßB2-crystallin, ßB1-crystallin, γD-crystallin, Hsp22, Hsp20, tau, alpha-synuclein, IAPP, beta-amyloid, PrP, huntingtin, calcitonin, atrial natriuretic factor, apolipoprotein AI, serum amyloid A, medin, prolactin, transthyretin, lysozyme, beta 2 microglobulin, gelsolin, keratoepithelin, cystatin, immunoglobulin light chain AL, and S-IBM.

Embodiment 30: The method of embodiments 28 or 29, wherein the protein is a protein underlying a loss of function disease.

Embodiment 31: The method of embodiment 30, wherein the protein underlying a loss of function disease is selected from the group consisting of mutant ß-glucosidase, cystic fibrosis transmembrane receptor, hexosaminidase A, hexosaminidase B, ß-galactosidase, and alpha-glucosidase.

Embodiment 32: A method of treating and/or preventing an eye disease or disorder in a subject in need thereof, comprising administering a therapeutically effective amount of the compound of any one of embodiments 1-22.

Embodiment 33: The method of embodiment 32, wherein the subject is having or at risk of developing an eye disease or disorder that affects the normal structure of the lens in the eye.

Embodiment 34: The method of embodiment 32 or 33, wherein the eye disease or disorder is selected from the group consisting of cataracts, congenital cataracts, cortical opacities, posterior subcapsular cataracts, presbyopia, nuclear sclerosis, retinal degenerative disorder, Refsum disease, Smith-Lemli-Opitz syndrome, Schnyder crystalline corneal dystrophy, drusen, age-related macular degeneration, and diabetic retinopathy.

Embodiment 35: The method of any one of embodiments 32-34, wherein the compound, or the pharmaceutically acceptable salt thereof, inhibits crystallin protein aggregation.

Embodiment 36: A method of treating cataract or blindness/impaired vision in a subject in need thereof, comprising administering a therapeutically effective amount of the compound of any one of embodiments 1-22.

Embodiment 37: The method of embodiment 36, wherein the compound dissolves the lens crystallin protein aggregate(s) in the eye of the subject.

Embodiment 38: The method of embodiment 37, wherein the lens crystallin protein aggregate is α-crystallin, ß-crystallin, or γ-crystallin.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating an eye disease or disorder in a subject in need thereof, comprising administering a therapeutically effective amount of a compound of Formula (Ic):

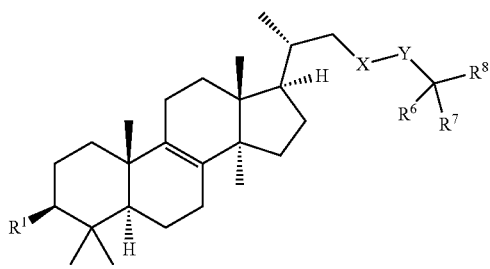

Formula (Ic)

or a pharmaceutically acceptable salt thereof,
wherein the eye disease or disorder is selected from the group consisting of cataracts, congenital cataracts, cortical opacities, posterior subcapsular cataracts, presbyopia, nuclear sclerosis, retinal degenerative disorder, Refsum disease, Smith-Lemli-Opitz syndrome, Schnyder crystalline corneal dystrophy, drusen, age-related macular degeneration, and diabetic retinopathy; and wherein X is —C($R^4$)$_2$—;
each $R^4$ is independently hydrogen, —OR$^e$, optionally substituted $C_1$-$C_6$alkyl, or halogen; each $R^e$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;
Y is —CH$_2$—, or —CH($R^5$)—;
$R^5$ is optionally substituted $C_1$-$C_6$alkyl or halogen;
$R^6$ and $R^7$ are each independently $C_1$-$C_3$alkyl;
$R^8$ is —OR$^h$, or —N($R^i$)$_2$;
$R^h$ is hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; each $R^i$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^i$ are taken together with the N atom to which they are attached to form an optionally substituted heterocycloalkyl ring;
$R^1$ is —OR$^{10}$, —SR$^{10}$, —N($R^{10}$)$_2$, or halogen; and each $R^{10}$ is independently hydrogen, optionally substituted $C_1$-$C_6$alkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycloalkyl ring.

2. The method of claim 1, wherein the subject is having or at risk of developing an eye disease or disorder that affects the normal structure of the lens in the eye.

3. The method of claim 1, wherein the compound, or the pharmaceutically acceptable salt thereof, inhibits crystallin protein aggregation.

4. The method of claim 3, wherein the protein is an amyloid-forming protein selected from Hsp27, αA-crystallin, αB-crystallin, ßB2-crystallin, ßB1-crystallin, γD-crystallin, Hsp22, Hsp20, tau, alpha-synuclein, IAPP, beta-amyloid, PrP, huntingtin, calcitonin, atrial natriuretic factor, apolipoprotein AI, serum amyloid A, medin, prolactin, transthyretin, lysozyme, beta 2 microglobulin, gelsolin, keratoepithelin, cystatin, immunoglobulin light chain AL, and S-IBM.

5. The method of claim 3, wherein the protein is a protein underlying a loss of function disease and is selected from the group consisting of mutant ß-glucosidase, cystic fibrosis transmembrane receptor, hexosaminidase A, hexosaminidase B, ß-galactosidase and alpha-glucosidase.

6. The method of claim 1, wherein X is —CH$_2$— or —CH(OR$^e$)—.

7. The method of claim 6, wherein $R^e$ is hydrogen.

8. The method of claim 1, wherein $R^5$ is —Br, —F, methyl, or ethyl.

9. The method of claim 1, wherein the compound has a formula of Formula (Id):

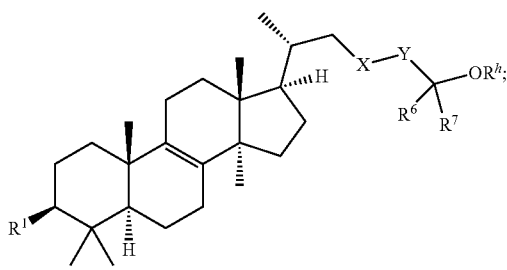

Formula (Id)

or the pharmaceutically acceptable salt thereof.

10. The method of claim 9, wherein $R^h$ is hydrogen.

11. The method of claim 1, wherein the compound, or the pharmaceutically acceptable salt thereof, is selected from:

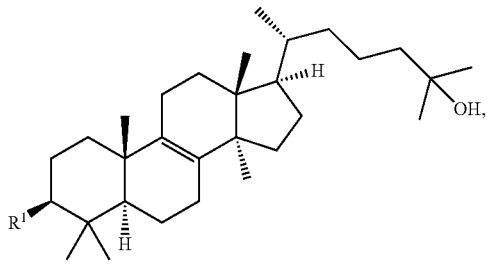

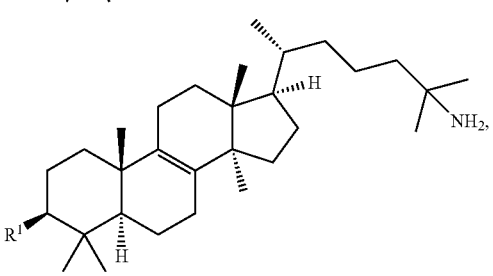

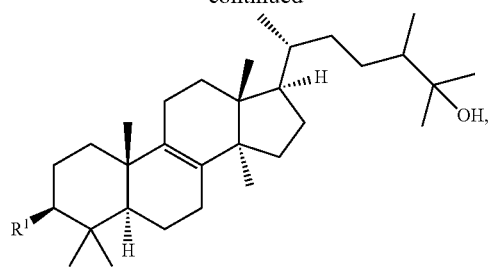
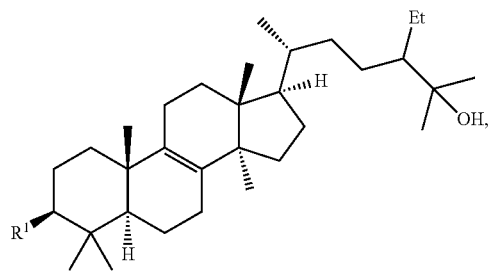
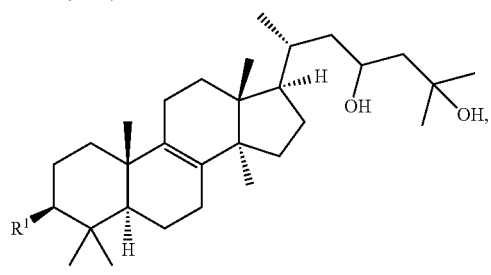
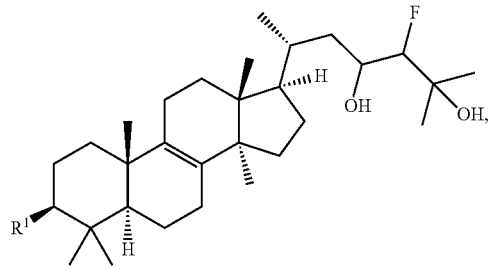
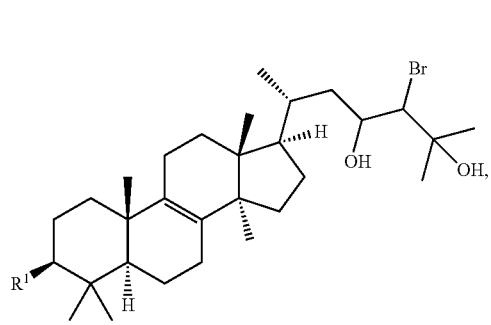
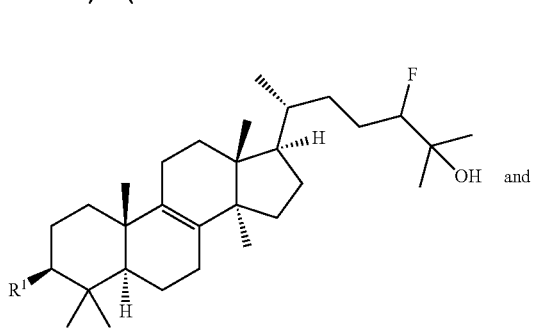
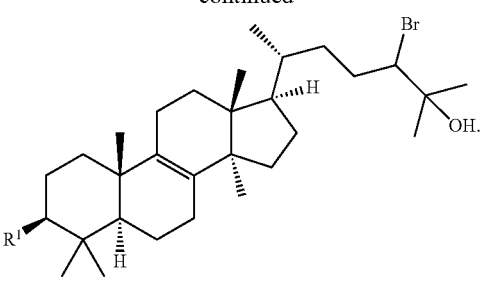
12. The method of claim 1, wherein $R^1$ is —$OR^{10}$.
13. The method of claim 12, wherein $R^1$ is —OH, —OMe, —OEt, or —O-n-Pr.
14. The method of claim 1, wherein $R^1$ is —$SR^{10}$ or —$N(R^{10})_2$.
15. The method of claim 1, wherein $R^1$ is halogen.
16. The method of claim 1, wherein the compound, or the pharmaceutically acceptable salt thereof, is selected from:
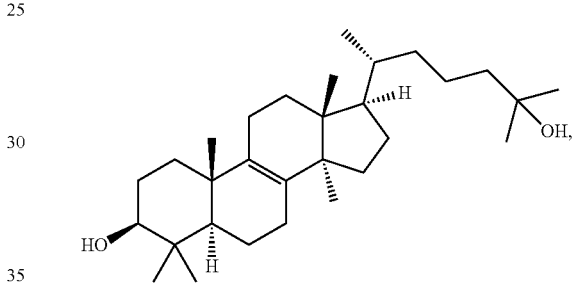
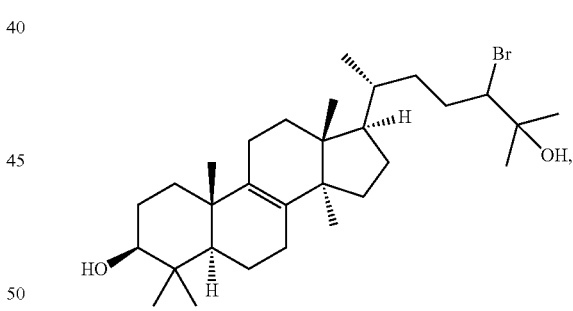
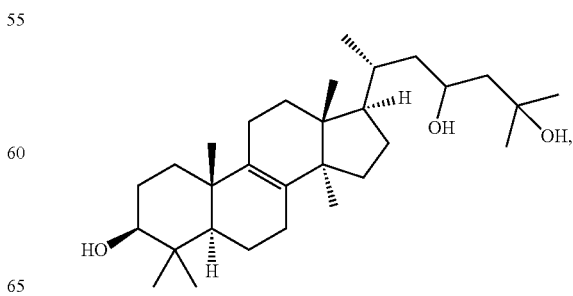

-continued

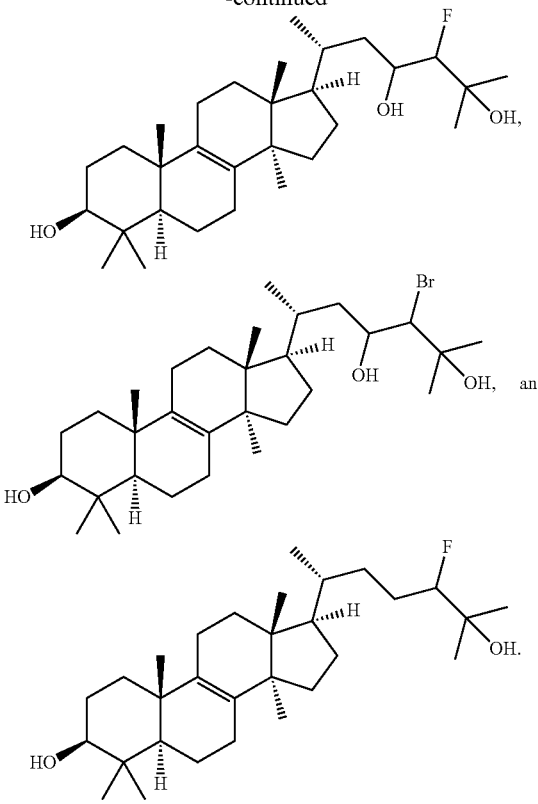

17. The method of claim 16, wherein the compound, or the pharmaceutically acceptable salt thereof, is selected from:

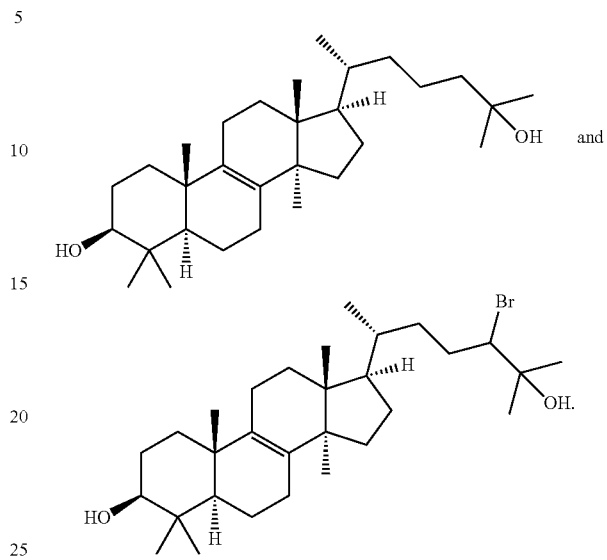

18. The method of claim 1, wherein the therapeutically effective amount of the compound, or the pharmaceutically acceptable salt thereof, is administered as a pharmaceutical composition; and wherein the pharmaceutical composition further comprises a pharmaceutically acceptable excipient.

* * * * *